(12) United States Patent
Kozel

(10) Patent No.: US 7,846,157 B2
(45) Date of Patent: Dec. 7, 2010

(54) METHOD AND APPARATUS FOR CONTROL OF ABLATION ENERGY AND ELECTROGRAM ACQUISITION THROUGH MULTIPLE COMMON ELECTRODES IN AN ELECTROPHYSIOLOGY CATHETER

(75) Inventor: Peter D. Kozel, Acton, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 1524 days.

(21) Appl. No.: 10/507,874

(22) PCT Filed: Mar. 17, 2003

(86) PCT No.: PCT/US03/08002

§ 371 (c)(1),
(2), (4) Date: May 16, 2005

(87) PCT Pub. No.: WO03/089997

PCT Pub. Date: Oct. 30, 2003

(65) Prior Publication Data

US 2005/0256521 A1  Nov. 17, 2005

Related U.S. Application Data

(60) Provisional application No. 60/364,546, filed on Mar. 15, 2002.

(51) Int. Cl.
*A61B 18/14* (2006.01)
*A61B 5/04* (2006.01)

(52) U.S. Cl. .......................................... 606/41; 600/374

(58) Field of Classification Search ............ 606/41; 600/374

See application file for complete search history.

(56) References Cited

U.S. PATENT DOCUMENTS 5,010,894 A * 4/1991 Edhag ........................ 607/128
5,239,999 A * 8/1993 Imran ........................ 600/374

(Continued)

FOREIGN PATENT DOCUMENTS

EP  1169976  1/2002

(Continued)

*Primary Examiner*—Lee S Cohen
(74) *Attorney, Agent, or Firm*—Wolf, Greenfield & Sacks, P.C.

(57) ABSTRACT

Method and apparatus for control of ablation energy and electrogram acquisition through multiple common electrodes in an electrophysiology catheter. A device that routes ablation energy to and that routes mapping signals received from an electrophysiology catheter having a plurality of conductive filaments including circuitry that provides, for each conductive filament when ablation energy is being delivered, an electrical signal path that has a low impedance for ablation energy and a high impedance for mapping signals. The device also includes circuitry that provides, for each conductive filament, when mapping signals are being received, an electrical signal path that has a high impedance for ablation energy and low impedance for mapping signals. At least one switch is provided that selectively groups electrodes into sectors for delivery of ablation energy.

10 Claims, 34 Drawing Sheets

U.S. PATENT DOCUMENTS

| | | | |
|---|---|---|---|
| 5,246,438 A * | 9/1993 | Langberg | 606/33 |
| 5,293,868 A * | 3/1994 | Nardella | 600/373 |
| 5,341,807 A | 8/1994 | Nardella | |
| 5,357,956 A * | 10/1994 | Nardella | 600/374 |
| 5,383,852 A | 1/1995 | Stevens-Wright | |
| 5,462,527 A | 10/1995 | Stevens-Wright | |
| 5,611,777 A | 3/1997 | Bowden | |
| 5,681,308 A | 10/1997 | Edwards et al. | |
| 6,178,354 B1 | 1/2001 | Gibson | |
| 6,315,778 B1 | 11/2001 | Gambale | |
| 2007/0088416 A1 * | 4/2007 | Atalar et al. | 607/115 |

FOREIGN PATENT DOCUMENTS

| | | |
|---|---|---|
| WO | WO 9406349 | 3/1994 |
| WO | WO 0182814 | 8/2001 |

* cited by examiner

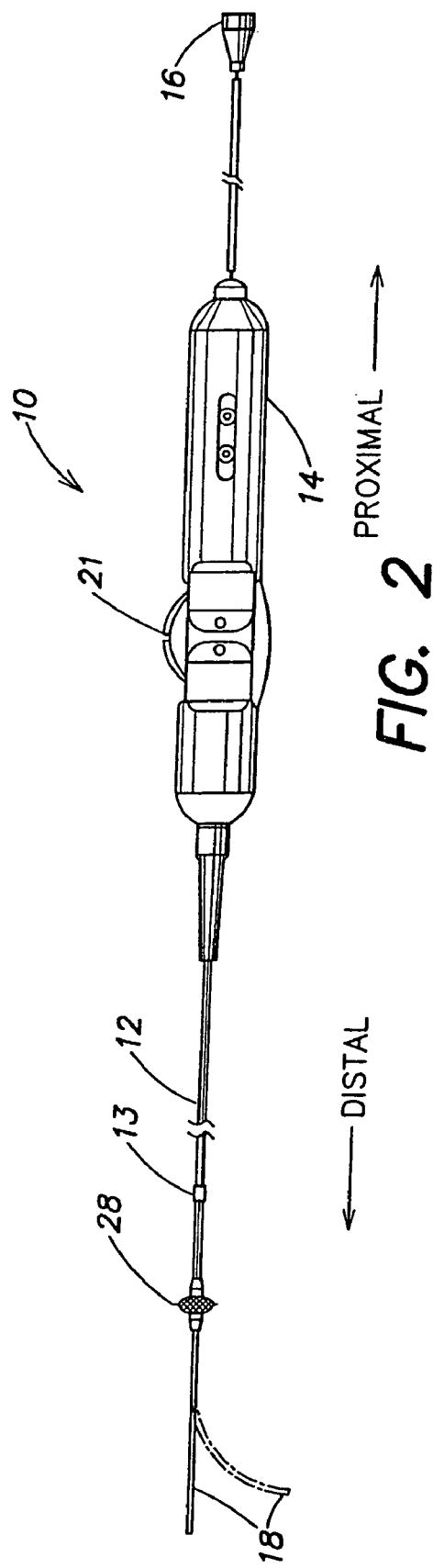
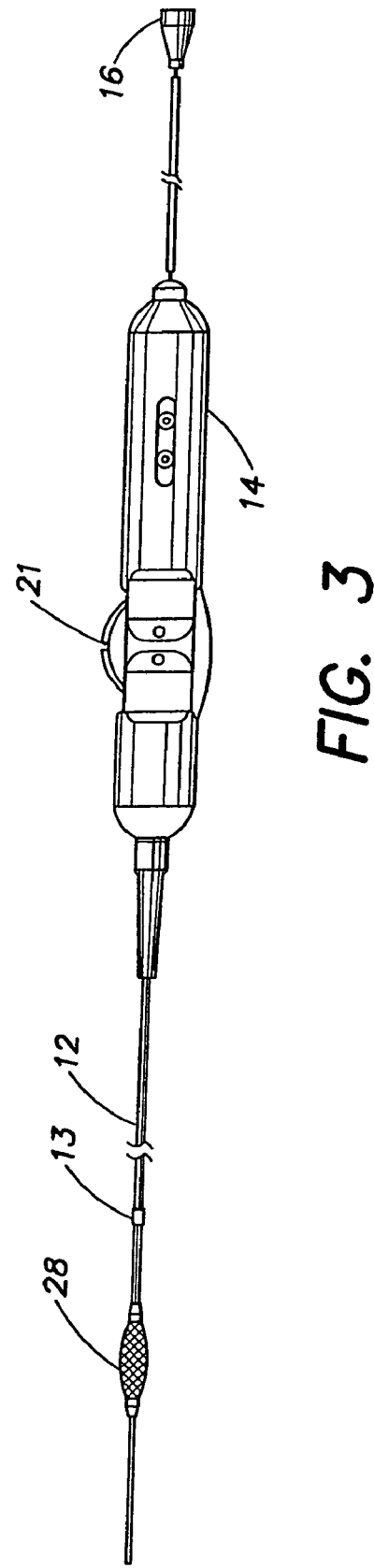
FIG. 2
FIG. 3

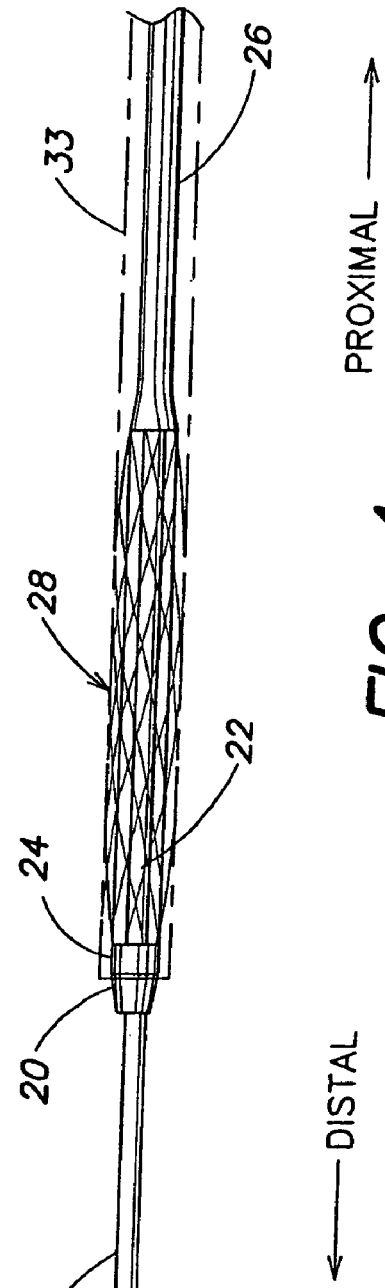
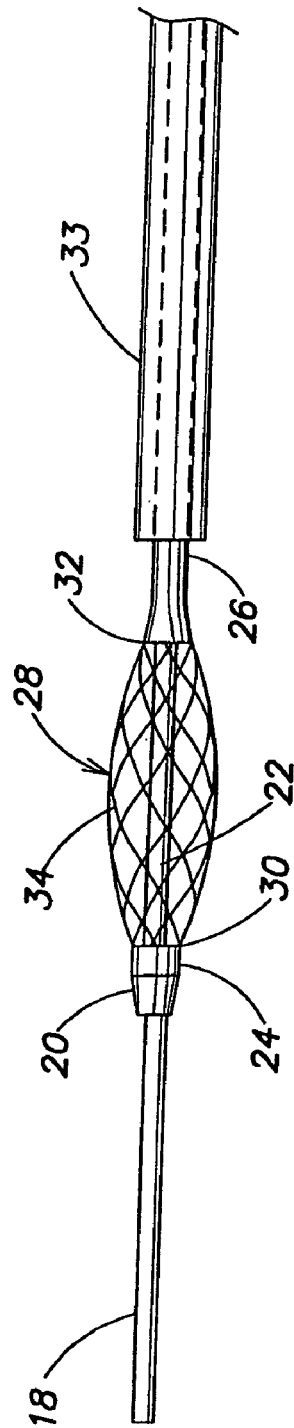
FIG. 4
FIG. 5

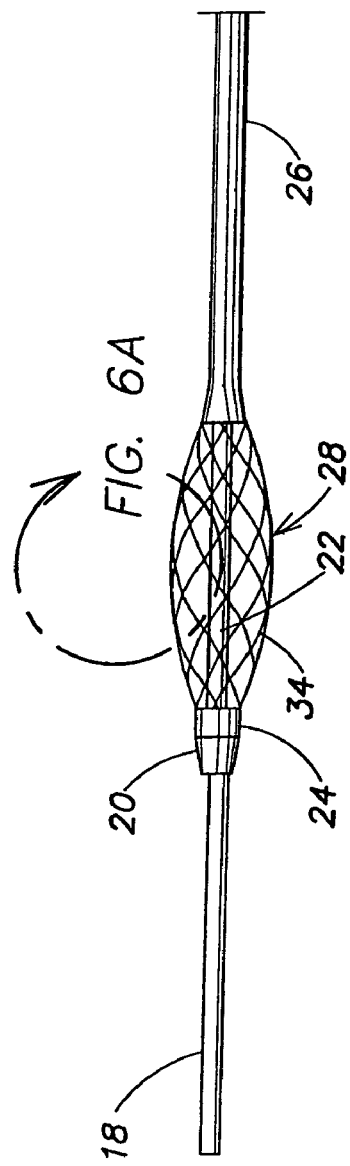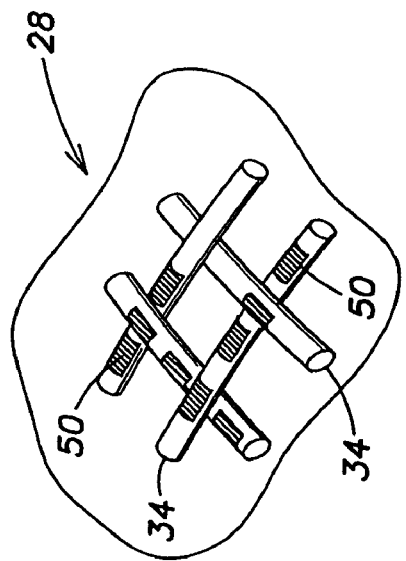
FIG. 6
FIG. 6A

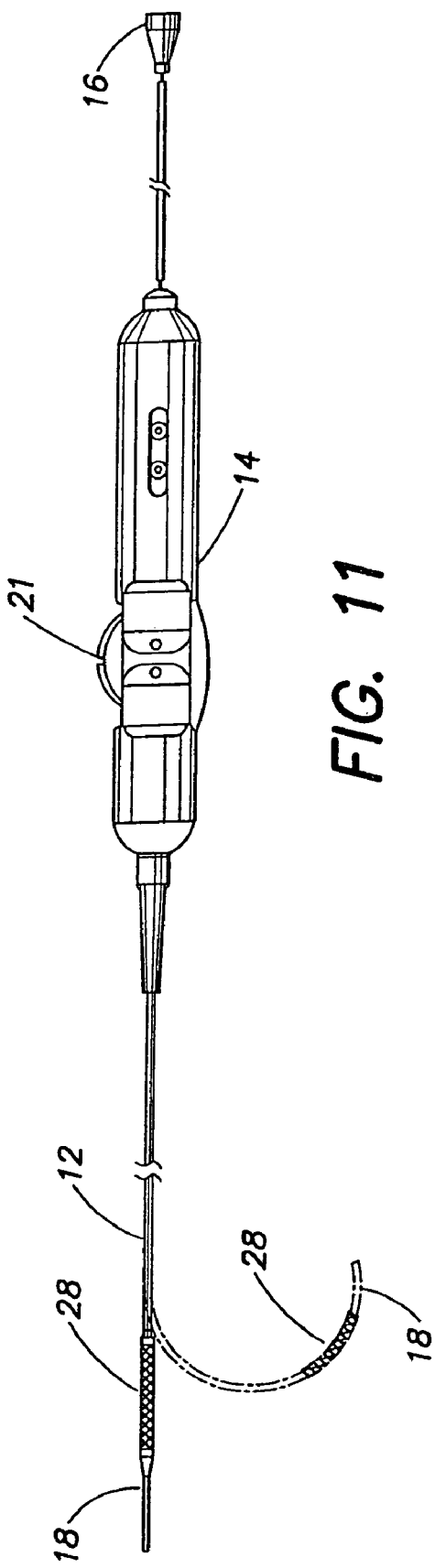
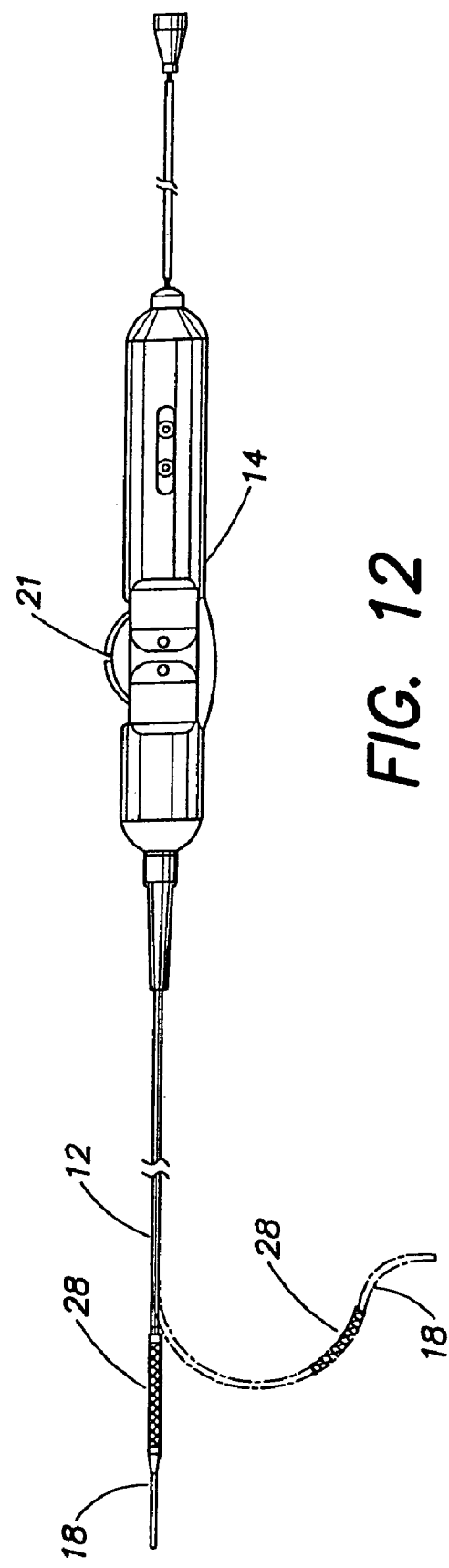
FIG. 11
FIG. 12

METHOD AND APPARATUS FOR CONTROL OF ABLATION ENERGY AND ELECTROGRAM ACQUISITION THROUGH MULTIPLE COMMON ELECTRODES IN AN ELECTROPHYSIOLOGY CATHETER

CROSS REFERENCE TO RELATED APPLICATIONS

This application claims the benefit, under 35 U.S.C. §365(c), of International Application No. PCT/US03/08002, filed Mar. 17, 2003, which in turn claims the benefit of U.S. provisional application Ser. No. 60/364,546, entitled "Method And Apparatus For Control Of Ablation Energy And Electrogram Acquisition Through Multiple Common Electrodes In An Electrophysiology Catheter" filed Mar. 15, 2002, which application is incorporated herein by reference in its entirety.

BACKGROUND OF THE INVENTION

1. Field of the Invention

The invention relates to medical devices for performing mapping and ablation procedures. More particularly, the invention relates to methods and apparatus for mapping and ablating at, in, or near, for example, the ostia of the pulmonary veins or coronary sinus, or any other blood vessel.

2. Discussion of the Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice. Another source of arrhythmias may be from reentrant circuits in the myocardium itself Such circuits may not necessarily be associated with vessel ostia, but may be interrupted by means of ablating tissue either within the circuit or circumscribing the region of the circuit. It should be noted that a complete 'fence' around a circuit or tissue region is not always required in order to block the propagation of the arrhythmia; in many cases simply increasing the propagation path length for a signal may be sufficient. Conventional means for establishing such lesion 'fences' include a multiplicity of point-by-point lesions, dragging a single electrode across tissue while delivering energy, or creating an enormous lesion intended to inactivate a substantive volume of myocardial tissue.

Commonly-owned U.S. patent application Ser. No. 09/396,502, entitled Apparatus For Creating A Continuous Annular Lesion, which is hereby incorporated by reference, discloses a medical device which is capable of ablating a continuous ring of tissue around the ostia of either veins or arteries leading to or from the atria.

SUMMARY OF THE INVENTION

The present invention encompasses apparatus and methods for mapping electrical activity within the heart. The present invention also encompasses methods and apparatus for creating lesions in the heart tissue (ablating) to create a region of necrotic tissue which serves to disable the propagation of errant electrical impulses caused by an arrhythmia.

In one embodiment, the invention provides a device for routing ablation energy to and for routing mapping signals received from an electrophysiology catheter having a plurality of conductive filaments, including circuitry that provides, for each conductive filament when ablation energy is being delivered, an electrical signal path that has a low impedance for ablation energy and a high impedance for mapping signals.

According to another embodiment, the invention further includes circuitry that provides, for each conductive filament, when mapping signals are being received, and electrical signal path that has a high impedance for ablation energy and low impedance for mapping signals.

According to another embodiment, the invention further includes switching circuitry for selectively coupling filaments in the electrophysiology catheter to a source of ablation energy.

According to another embodiment, the switching circuitry selectively couples sectors of filaments to a source of ablation energy.

According to another embodiment, there are four sectors.

According to another embodiment, the switching circuitry selectively couples approximately a first half of the filaments in the electrophysiology catheter to a source of ablation energy.

According to another embodiment, the switching circuitry selectively couples approximately a second half of the filaments in the electrophysiology catheter to a source of ablation energy.

According to another embodiment, the first half of the filaments is interleaved with the second half of the filaments.

According to another embodiment, the circuitry comprises a capacitor in the electrical signal path of each conductive filament.

According to another embodiment, the invention further includes a resistor respectively coupled to each conductive filament.

According to another embodiment, the invention provides a catheter system comprising an electrophysiology catheter, an ablation energy generator, a recording device, and a device for routing ablation energy to and for routing mapping signals received from an electrophysiology catheter having a plurality of conductive filaments, comprising circuitry that provides, for each conductive filament when ablation energy is being delivered, an electrical signal path that has a low impedance for ablation energy and a high impedance for mapping signals that couples the electrophysiology catheter to the ablation energy generator and the recording device.

The features and advantages of the present invention will be more readily understood and apparent from the following detailed description of the invention, which should be read in conjunction with the accompanying drawings, and from the claims which are appended at the end of the Detailed Description.

BRIEF DESCRIPTION OF THE DRAWINGS

In the drawings, which are incorporated herein by reference and in which like elements have been given like references characters.

FIGS. 2 and 3 illustrate further details of the catheter illustrated in FIG. 1;

FIGS. 4-7 illustrate further details of the braided conductive member illustrated in FIGS. 2 and 3;

FIGS. 11-13 illustrate further details of the steering capabilities of the present invention;

DETAILED DESCRIPTION

System Overview

Figure 1:
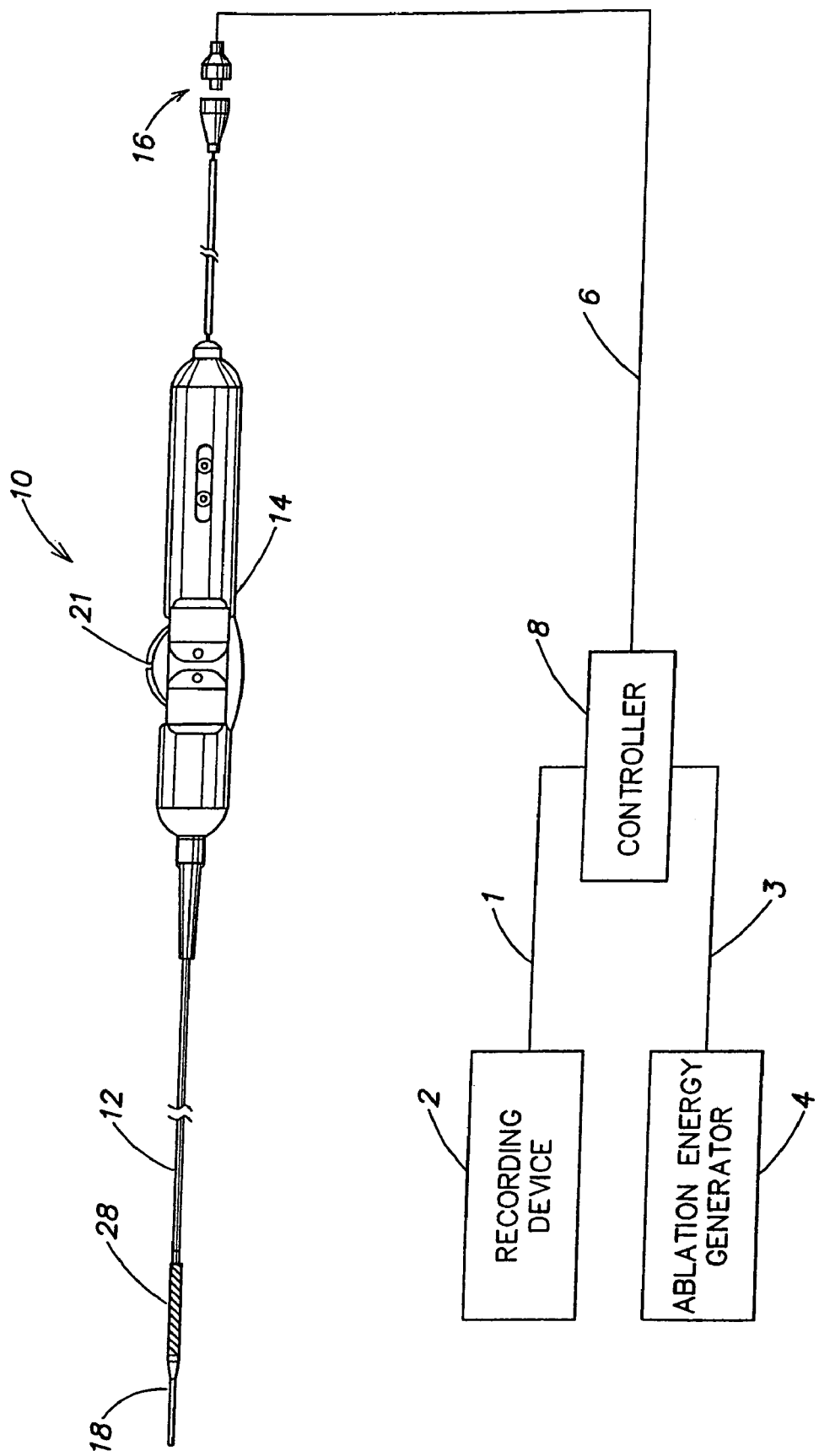
FIG. 1 illustrates an overview of a mapping and ablation catheter system in accordance with the present invention.
Figure 7:
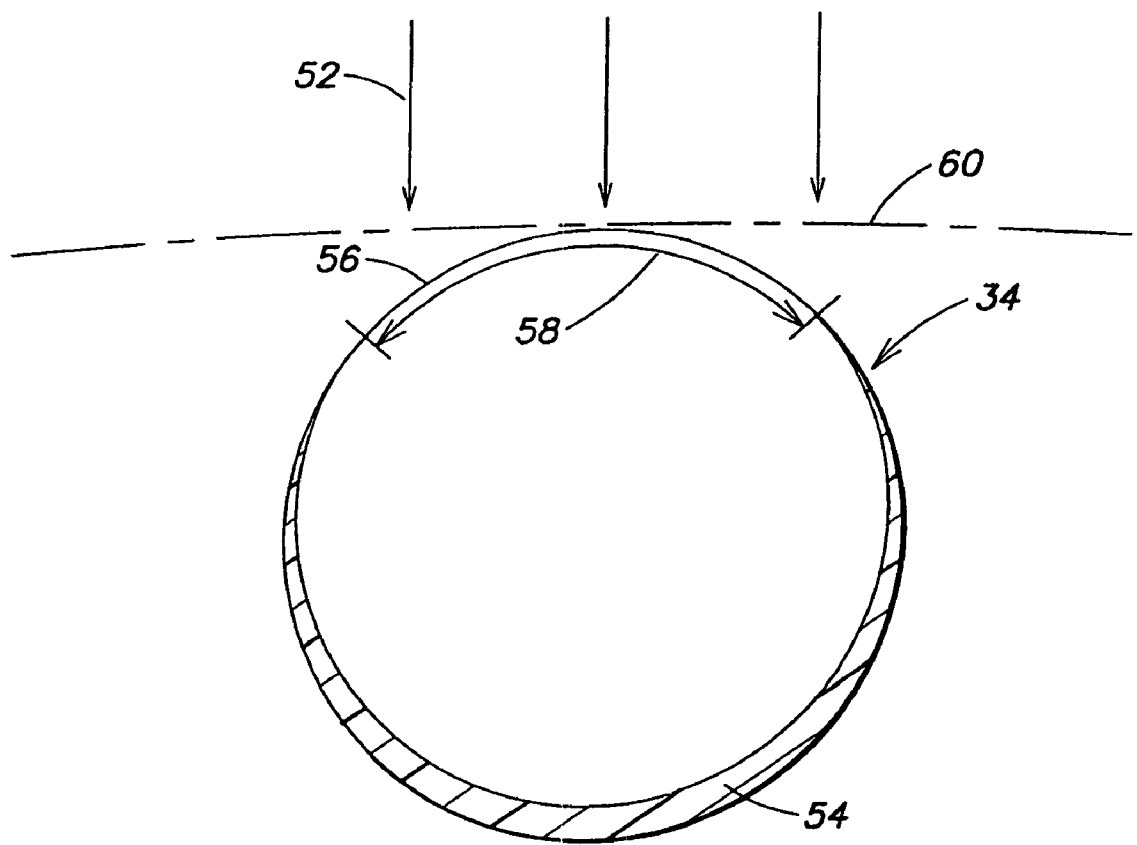

Reference is now made to FIG. 1, which figure illustrates an overview of a mapping and ablation catheter system in accordance with the present invention. The system includes a catheter 10 having a shaft portion 12, a control handle 14, and a connector portion 16. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided by ablation energy generator 4 to catheter 10. When used in a mapping application, controller 8 is used to process signals coming from catheter 10 and to provide these signals to recording device 2. Although illustrated as separate devices, recording device 2, ablation energy generator 4, and controller 8 could be incorporated into a single device. In one embodiment, controller 8 may be a QUADRAPULSE RF CONTROLLER™ device available from CR Bard, Inc., Murray Hill, N.J. In one embodiment, recording device 2 may be a LAB system device available from CR Bard, Inc., Murray Hill, N.J.

In this description, various aspects and features of the present invention will be described. The various features of the invention are discussed separately for clarity. One skilled in the art will appreciate that the features may be selectively combined in a device depending upon the particular application. Furthermore, any of the various features may be incorporated in a catheter and associated method of use for either mapping or ablation procedures.

Catheter Overview

Reference is now made to FIGS. 2-7, which figures illustrate one embodiment of the present invention. The present invention generally includes a catheter and method of its use for mapping and ablation in electrophysiology procedures. Catheter 10 includes a shaft portion 12, a control handle 14, and a connector portion 16. When used in mapping applications, connector portion 16 is used to allow signal wires running from the electrodes at the distal portion of the catheter to be connected to a device for processing the electrical signals, such as a recording device.

Catheter 10 may be a steerable device. FIG. 2 illustrates the distal tip portion 18 being deflected by the mechanism contained within control handle 14. Control handle 14 may include a rotatable thumb wheel which can be used by a user to deflect the distal end of the catheter. The thumb wheel (or any other suitable actuating device) is connected to one or more pull wires which extend through shaft portion 12 and are connected to the distal end 18 of the catheter at an off-axis location, whereby tension applied to one or more of the pull wires causes the distal portion of the catheter to curve in a predetermined direction or directions. U.S. Pat. Nos. 5,383, 852, 5,462,527, and 5,611,777, which are hereby incorporated by reference, illustrate various embodiments of control handle 14 that may be used for steering catheter 10.

Shaft portion 12 includes a distal tip portion 18, a first stop 20 and an inner member 22 connected to the first stop portion 20. Inner member 22 may be a tubular member. Concentrically disposed about inner member 22 is a first sheath 24 and a second sheath 26. Also concentrically disposed about inner member 22 is a braided conductive member 28 anchored at respective ends 30 and 32 to the first sheath 24 and the second sheath 26, respectively.

In operation, advancing the second sheath 26 distally over inner member 22 causes the first sheath 24 to contact stop 20. Further distal advancement of the second sheath 26 over inner member 22 causes the braided conductive member 28 to expand radially to assume various diameters and/or a conical shape. FIG. 3 illustrates braided conductive member 28 in an unexpanded (collapsed or "undeployed") configuration.

FIGS. 2 and 4 illustrate braided conductive member 28 in a partially expanded condition. FIG. 1 illustrates braided conductive member 28 radially expanded ("deployed") to form a disk.

Alternatively, braided conductive member 28 can be radially expanded by moving inner member 22 proximally with respect to the second sheath 26.

As another alternative, inner member 22 and distal tip portion 18 may be the same shaft and stop 20 may be removed. In this configuration, sheath 24 moves over the shaft in response to, for example, a mandrel inside shaft 22 and attached to sheath 24 in the manner described, for example, in U.S. Pat. No. 6,178,354, which is incorporated herein by reference.

As illustrated particularly in FIGS. 4 and 5 a third sheath 33 may be provided. The third sheath serves to protect shaft portion 12 and in particular braided conductive member 28 during manipulation through the patient's vasculature. In addition, the third sheath 33 shields braided conductive member 28 from the patient's tissue in the event ablation energy is prematurely delivered to the braided conductive member 28.

The respective sheaths 24, 26, and 33 can be advanced and retracted over the inner member 22, which may be a tubular member, in many different manners. Control handle 14 may be used. U.S. Pat. Nos. 5,383,852, 5,462,527, and 5,611,777 illustrate examples of control handles that can control sheaths 24, 26, and 33. As described in these incorporated by reference patents, control handle 14 may include a slide actuator which is axially displaceable relative to the handle. The slide actuator may be connected to one of the sheaths, for example, the second sheath 26 to control the movement of the sheath 26 relative to inner member 22, to drive braided conductive member 28 between respective collapsed and deployed positions, as previously described. Control handle 14 may also include a second slide actuator or other mechanism coupled to the retractable outer sheath 33 to selectively retract the sheath in a proximal direction with respect to the inner member 22.

Braided conductive member 28 is, in one embodiment of the invention, a plurality of interlaced, electrically conductive filaments 34. Braided conductive member 28 may be a wire mesh. The filaments are flexible and capable of being expanded radially outwardly from inner member 22. The filaments 34 are preferably formed of metallic elements having relatively small cross sectional diameters, such that the filaments can be expanded radially outwardly. The filaments may be round, having a dimension on the order of about 0.001-0.030 inches in diameter. Alternatively, the filaments may be flat, having a thickness on the order of about 0.001-0.030 inches, and a width on the order of about 0.001-0.030 inches. The filaments may be formed of Nitinol type wire. Alternatively, the filaments may include non metallic elements woven with metallic elements, with the non metallic elements providing support to or separation of the metallic elements. A multiplicity of individual filaments 34 may be provided in braided conductive member 28, for example up to 300 or more filaments.

Each of the filaments 34 can be electrically isolated from each other by an insulation coating. This insulation coating may be, for example, a polyamide type material. A portion of the insulation on the outer circumferential surface 60 of braided conductive member 28 is removed. This allows each of the filaments 34 to form an isolated electrode, not an electrical contact with any other filament, that may be used for mapping and ablation. Alternatively, specific filaments may be permitted to contact each other to form a preselected grouping.

Each of the filaments 34 is helically wound under compression about inner member 22. As a result of this helical construction, upon radial expansion of braided conductive member 28, the portions of filaments 34 that have had the insulation stripped away do not contact adjacent filaments and thus, each filament 34 remains electrically isolated from every other filament. FIG. 6, in particular, illustrates how the insulation may be removed from individual filaments 34 while still providing isolation between and among the filaments. As illustrated in FIG. 6, regions 50 illustrate regions, on the outer circumferential surface 60 of braided conductive member 28, where the insulation has been removed from individual filaments 34. In one embodiment of the invention, the insulation may be removed from up to one half of the outer facing circumference of each of the individual filaments 34 while still retaining electrical isolation between each of the filaments 34.

The insulation on each of the filaments 34 that comprise braided conductive member 28 may be removed about the outer circumferential surface 60 of braided conductive member 28 in various ways. For example, one or more circumferential bands may be created along the length of braided conductive member 28. Alternatively, individual sectors or quadrants only may have their insulation removed about the circumference of braided conductive member 28. Alternatively, only selected filaments 34 within braided conductive member 28 may have their circumferentially facing insulation removed. Thus, an almost limitless number of configurations of insulation removal about the outer circumferential surface 60 of braided conductive member 28 can be provided depending upon the mapping and ablation characteristics and techniques that a clinician desires.

The insulation on each of the filaments 34 may be removed at the outer circumferential surface 60 of braided conductive member 28 in a variety of ways as long as the insulation is maintained between filaments 34 so that filaments 34 remain electrically isolated from each other.

The insulation can be removed from the filaments 34 in a variety of ways to create the stripped portions 50 on braided conductive member 28. For example, mechanical means such as abration or scraping may be used. In addition, a water jet, chemical means, or thermal radiation means may be used to remove the insulation.

In one example of insulation removal, braided conductive member 28 may be rotated about inner member 22, and a thermal radiation source such as a laser may be used to direct radiation at a particular point along the length of braided conductive member 28. As the braided conductive member 28 is rotated and the thermal radiation source generates heat, the insulation is burned off the particular region.

Insulation removal may also be accomplished by masking selected portions of braided conductive member 28. A mask, such as a metal tube may be placed over braided conductive member 28. Alternatively, braided conductive member 28 may be wrapped in foil or covered with some type of photoresist. The mask is then removed in the areas in which insulation removal is desired by, for example, cutting away the mask, slicing the foil, or removing the photoresist. Alternatively, a mask can be provided that has a predetermined insulation removal pattern. For example, a metal tube having cutouts that, when the metal tube is placed over braided conductive member 28, exposes areas where insulation is to be removed.

FIG. 6 illustrates how thermal radiation 52 may be applied to the outer circumferential surface 56 of a respective filament 34 that defines the outer circumferential surface 60 of braided conductive member 28. As thermal radiation 52 is applied, the insulation 54 is burned off or removed from the outer circumference 56 of wire 34 to create a region 58 about the circumference 56 of filament 34 that has no insulation.

The insulation 54 can also be removed in a preferential manner so that a particular portion of the circumferential surface 56 of a filament 34 is exposed. Thus, when braided conductive member 28 is radially expanded, the stripped portions of filaments may preferentially face the intended direction of mapping or ablation.

Although removal of insulation from filaments 34 in the vicinity of the outer circumferential surface 60 has been discussed in detail above, insulation can be removed from one or more filaments 34 that comprise braided conductive member 28 anywhere along the length of the filament. For example, as illustrated in U.S. Pat. No. 6,315,778, which is incorporated herein by reference, braided conductive member 28 may be expanded so that it forms a distal-facing ring. In this configuration, the insulation may be removed from filaments 34 in the vicinity of the distal-facing ring. In another embodiment, braided conductive member 28 may be expanded so that it forms a proximal-facing ring and insulation may be removed in the vicinity of the proximal-facing ring. Insulation may be selectively removed to define mapping and/or ablation filaments anywhere on the proximal side, distal side, or circumferential surface of braided conductive member 28 when in its expanded or deployed configuration.

With the insulation removed from the portions of filaments 34 on the outer circumferential surface 60 of braided conductive member 28, a plurality of individual mapping and ablation channels can be created. A wire runs from each of the filaments 34 within catheter shaft 12 and control handle 14 to connector portion 16. A multiplexer or switch box may be connected to the conductors so that each filament 34 may be controlled individually. This function may be incorporated into controller 8. A number of filaments 34 may be grouped together for mapping and ablation. Alternatively, each individual filament 34 can be used as a separate mapping channel for mapping individual electrical activity within a blood vessel at a single point. Using a switch box or multiplexer to configure the signals being received by filaments 34 or ablation energy sent to filaments 34 results in an infinite number of possible combinations of filaments for detecting electrical activity during mapping procedures and for applying energy during an ablation procedure.

The ability to individually define a filament 34 as a mapping or ablation channel may be combined with selective insulation removal from a filament to create a wide variety of mapping/ablation configurations. For example, insulation may be removed from a number of filaments to create an ablative ring around the outer circumferential surface of braided conductive member 28 and insulation may be selectively removed from another filament on the proximal and/or distal side of a filament that is inside the ablative ring but electrically insulated from the filaments forming the ablative ring to define a mapping channel. This can allow a user to ablate tissue in contact with the ring and then check for electrical activity inside the ring using the filament defined as the mapping channel before, during, and/or after an ablation operation. In another embodiment, the ablative ring can be formed inside a mapping channel to allow checking electrical activity outside the ablative ring. These configurations can also be combined to provide an outer mapping channel or channels outside the ablative ring, and ablation ring (or element), and an inner mapping channel or channels inside the ablation ring or element concentrically arranged about the catheter shaft.

In accordance with the invention, a single catheter that provides both mapping and ablation functions can reduce the number of catheter changes needed during an electrophysiology procedure and can allow feedback simultaneously with or shortly after ablation to determine the effectiveness of an ablation operation.

By controlling the amount of insulation that is removed from the filaments 34 that comprise braided conductive member 28, the surface area of the braid that is in contact with a blood vessel wall can also be controlled. This in turn will allow control of the impedance presented to an ablation energy generator, for example, generator 4. In addition, selectively removing the insulation can provide a predetermined or controllable profile of the ablation energy delivered to the tissue.

The above description illustrates how insulation may be removed from a filaments 34. Alternatively, the same features and advantages can be achieved by adding insulation to filaments 34. For example, filaments 34 may be bare wire and insulation can be added to them.

Individual control of the electrical signals received from filaments 34 allows catheter 10 to be used for bipolar (differential or between filament) type mapping as well as unipolar (one filament with respect to a reference) type mapping.

Catheter 10 may also have, as illustrated in FIGS. 2 and 3, a reference electrode 13 mounted on shaft 12 so that reference electrode 13 is located outside the heart during unipolar mapping operations.

Radiopaque markers can also be provided for use in electrode orientation and identification.

One skilled in the art will appreciate all of the insulation can be removed from filaments 34 to create a large ablation electrode.

Although a complete catheter steerable structure has been illustrated, the invention can also be adapted so that inner tubular member 22 is a catheter shaft, guide wire, or a hollow tubular structure for introduction of saline, contrast media, heparin or other medicines, or introduction of guidewires, or the like.

Temperature Sensing

A temperature sensor or sensors, such as, but not limited to, one or more thermocouples may be attached to braided conductive member 28 for temperature sensing during ablation procedures. A plurality of thermocouples may also be woven into the braided conductive member 28. An individual temperature sensor could be provided for each of the filaments 34 that comprise braided conductive member 28. Alternatively, braided conductive member 28 can be constructed of one or more temperature sensors themselves.

Figure 8:
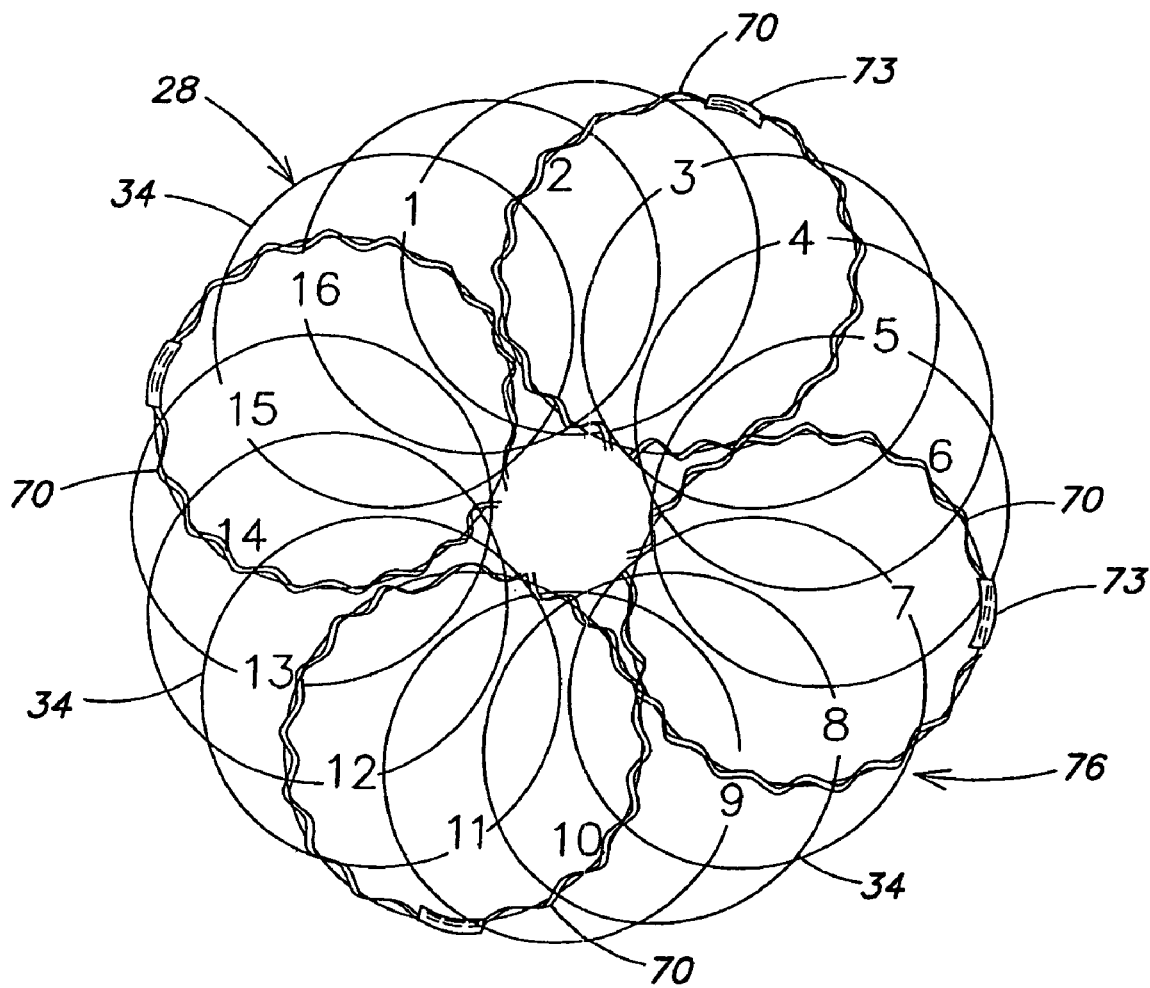
FIGS. 8-10A illustrate, among other things, temperature sensing in the present invention.

FIG. 8 illustrates braided conductive member 28 in its fully expanded or deployed configuration. Braided conductive member 28 forms a disk when fully expanded. In the embodiment illustrated in FIG. 8, there are sixteen filaments 34 that make up braided conductive member 28.

Temperature monitoring or control can be incorporated into braided conductive member 28, for example, by placing temperature sensors (such as thermocouples, thermistors, etc.) on the expanded braided conductive member 28 such that they are located on the distally facing ablative ring formed when braided conductive member 28 is in its fully expanded configuration. "Temperature monitoring" refers to temperature reporting and display for physician interaction. "Temperature control" refers to the capability of adding an algorithm in a feedback loop to titrate power based on temperature readings from the temperature sensors disposed on braided conductive member 28. Temperature sensors can provide a means of temperature control provided the segment of the ablative ring associated with each sensor is independently controllable (e.g., electrically isolated from other regions of the mesh). For example, control can be achieved by dividing the ablative structure into electrically independent sectors, each with a temperature sensor, or alternatively, each with a mechanism to measure impedance in order to facilitate power titration. The ablative structure may be divided into electrically independent sectors so as to provide zone control. The provision of such sectors can be used to provide power control to various sections of braided conductive member 28.

Figure 9:
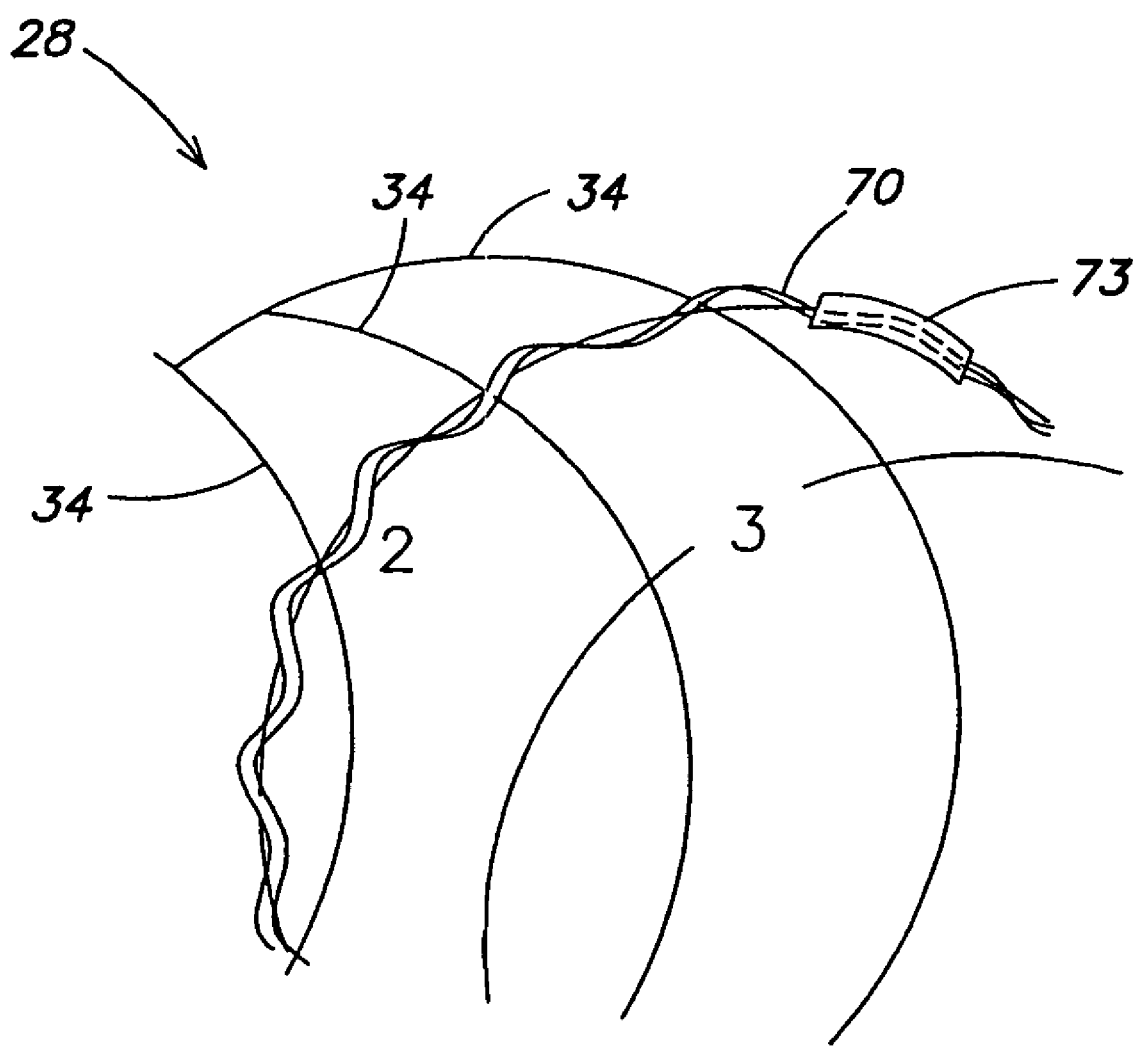

As illustrated in FIGS. 8-9, four temperature sensors 70 are provided on braided conductive member 28. As noted previously, since the individual filaments 34 in braided conductive member 28 are insulated from each other, a number of independent sectors may be provided. A sector may include one or more filaments 34. During ablation procedures, energy can be applied to one or more of the filaments 34 in any combination desired depending upon the goals of the ablation procedure. A temperature sensor could be provided on each filament 34 of braided conductive member 28 or shared among one or more filaments. In mapping applications, one or more of the filaments 34 can be grouped together for purposes of measuring electrical activity. These sectoring functions can be provided in controller 8.

Reference is now made to FIGS. 25A-25D, which figures illustrate control circuitry 500 that may be incorporated in controller 8 or provided separately in a separate device that can be connected to controller 8 to allow RF ablation energy delivery and intracardiac electrogram acquisition through multiple common filaments 34 contained within the braided conductive member 28. Control circuitry 500 can allow ablation energy delivery with simultaneous intracardiac electrogram acquisition. In particular, the control circuitry 500 illustrated in FIGS. 25A-25D provides one example embodiment for providing sectoring functions of the filaments 34 in braided conductive member 28.

In one example, 36 individual filaments 34 comprising braided conductive member 28 are routed though the catheter to the control circuitry 500 illustrated in FIGS. 25A-25D. The filament circuits are then divided into four groups 502, 504, 506, and 508 of nine filaments each (quadrants), each quadrant representing 90° of the circumference of braided conductive member 28. Those nine circuits are again combined to form a single node for input to one channel of controller 8. The control circuitry is used in each of circuits 502, 504, 506, and 508 to form a total of four quadrants and four channels.

Without the control circuitry 500, the nine filament wires comprising each ablation channel could effectively represent a short circuit. Since no signal can be measured across a short circuit, electrogram acquisition from filaments within a given quadrant may not be possible (this is true any time multiple filaments of braided conductive member 28 are connected to a common node).

Accordingly, control circuitry 500 provides the necessary impedance (isolation) between filaments that allows voltage to develop between them and thus a signal to be extracted. However, simultaneous ablation through those same filaments 34 requires a low impedance path from the catheter to the patient so that the energy intended for tissue destruction is not otherwise wasted. In other words, the amount of impedance necessary for signal acquisition precludes ablation energy delivery. However, because ablation and electrogram frequencies are very different, the use of control circuitry 500 allows both requirements to be met by the introduction of capacitance in the circuit that has frequency dependent characteristics. Thus, a capacitor can be selected such that at ablation frequencies the impedance appears as a short circuit but at electrogram frequencies, the impedance is sufficient to develop the necessary voltage for signal acquisition.

The impedance (reactance) of an ideal capacitor follows the following formula:

$$X_c, \text{capacitive reactance}, = 1/2\pi fC$$

Where C=capacitance
f=frequency

Note the following:
 Ablation frequency is typically 500 kHz
 Ablation impedance for this catheter type is 150-400Ω per individual wire
 Electrogram (mapping) frequency range is 30-1000 Hz
 Inter-wire impedance of the illustrated catheter having a braided or mesh conductive member at electrogram frequencies is typically 400-1300Ω

A capacitance value is desired such that at 500 kHz (typical frequency of ablation energy) its impedance is much less than 50Ω and is greater than 100Ω at 100 Hz (typical mapping frequency).

Using the above relationships and constraints:
Ideally $X_c$ should be as low as possible for ablation. Choosing $X_c$ as 5Ω so that the loss of ablation energy is limited:

$$C > 1/2\pi f X_c = 1/2\pi (500 \text{ kHz})(1\Omega) = 0.064 \, \mu F$$

and

An impedance of 2kΩ has been shown to be sufficient to ensure adequate electrogram (mapping) amplitude and since most energy contained in an intracardiac electrogram is below 500 Hz choose C such that:

$$C < 1/2\pi f X_c = 1/2\pi (500 \text{ Hz})(2\text{k}\Omega) = 0.16 \, \mu F$$

to reduce amplitude attenuation while retaining high frequency response.

In one embodiment, the value of capacitors C1-C36 was chosen to be 0.068 µF, fulfilling both performance goals.

Additionally, the control circuitry 500 contains a resistor array (resistors R1-R36) with one each available to every filament wire with the other ends terminated to a common node UNI-REF. That common node provides a virtual electrical null point (average) against which unipolar electrogram channels can be formed. Resistors R1-R36 have a typical value of 10 kΩ. The presence and operation of the resistor network is separate and independent from the frequency selective characteristics control circuitry 500.

The principles detailed above can be adapted and applied to other catheters, electrode configurations and energy delivery schemes.

Reference is now made to FIGS. 29 and 30A-30D, which illustrate another embodiment of the switching circuitry. In contrast to the circuitry illustrated in FIGS. 25A-25D, switching circuitry 600 in FIGS. 29 and 30A-30D differs in the way the filaments 34 are grouped. In the embodiment illustrated in FIGS. 29A and 30A-30D, filaments are grouped into quadrants comprising eight filaments, rather than the nine filament configuration illustrated in FIGS. 25A-25D. Each of the eight filaments are combined into groups of two filaments, for example, 34-1, 34-2; 34-3, 344; 34-5, 34-6; etc.

As noted, eight filaments 34 comprise a quadrant in the embodiment illustrated in FIGS. 29 and 30A-30D. The ninth filament in each sector, namely, 34-9 in sector 1, 34-10 in sector 2, 34-27 in sector 3, and 34-28 in sector 4 are not used in this embodiment because of proximity effects. Proximity effects cause the energy on a filament to interfere with the energy being delivered on an adjacent filament. Proximity effects are especially exacerbated at an edge of a sector.

Therefore, to avoid deleterious effects, eight filaments, rather than nine, are combined into a sector in the embodiment illustrated in FIGS. 29 and 30A-30D.

In the illustrated embodiment, ablation energy generator 4 has four individual channels capable of delivering ablation energy. Channels 1 and 2 are coupled to switches SW1 and SW2. Channels 3 and 4 are coupled to switches SW3 and SW4. To avoid proximity effects, only four filaments (two groups of two filaments) are activated at any time and these two groups are chosen to be balanced and as far away from each other as possible. For example, activating SW1 causes filaments 34-1, 34-2 and 34-5, 34-6 to be coupled to channel 1 of ablation energy generator 4. Activating SW1 also causes filaments 34-3, 344 and 34-7, 34-8 to be coupled to channel 2 of ablation energy generator 4. Thereafter, ablation energy generator 4 is controlled to deliver ablation energy to filaments 34-1, 34-2; 34-5, 34-6 during a first time period and to filaments 34-2, 34-4; 34-7, 34-8 during a second time period.

One skilled in the art will appreciate that the operation of switches SW2, SW3, and SW4 is analogous to the operation of switch SW1 for the remaining quadrants that comprise braided mesh conductor 28.

One skilled in the art will also appreciate that the filaments, switching, and delivery of ablation energy may be organized in other ways depending on, for example, the results desired and the particular ablation energy generator used.

The circuitry illustrated in FIGS. 29 and 30A-30D provides an additional mode of operation when delivering ablation energy to filaments 34. An additional switch SW5 is provided. Switch SW5 is connected to each respective group of two filaments in the catheter. In one mode of operation, switch 5 may be used to activate all eighteen pairs of filaments 34 to provide for circumferential delivery of ablation energy. Alternatively, switch 5 can selectively group the eighteen pairs of filaments. In one embodiment, the eighteen pairs of filaments 34 are divided into two interleaved helixes formed by alternating pairs of filaments 34. For example, a first helix may be formed of filaments 34-1, 34-2; 34-5, 34-6; . . . 34-33, 34-34. A second helix may be formed of filaments 34-3, 344; 34-7, 34-9; . . . 34-35, 34-36. Each of the respective two helixes can be independently and alternately activated to deliver ablation energy when carrying out a circumferential ablation procedure around the inner parameter of a blood vessel. Thus, a first helix H1 includes nine of the eighteen groups of filaments 34 and the second helix H2 includes the remaining nine of eighteen pairs of filaments 34.

In all other respects, the circuitry illustrated in FIGS. 29 and 30A-30D operates as described in connection with FIGS. 25A-25D.

One skilled in the art will appreciate that the switching circuitry illustrated in FIGS. 29 and 30A-30D can be active electronic components, such as multiplexers or electronic switches, or may be passive components such as conventional mechanical switches. One skilled in the art will also appreciate that the selective switching of filaments 34 as illustrated in particular FIGS. 25A-25D, 29, and 30A-30D is illustrative and there can be many other combinations of filaments depending upon the procedure and effect desired.

Figure 10:
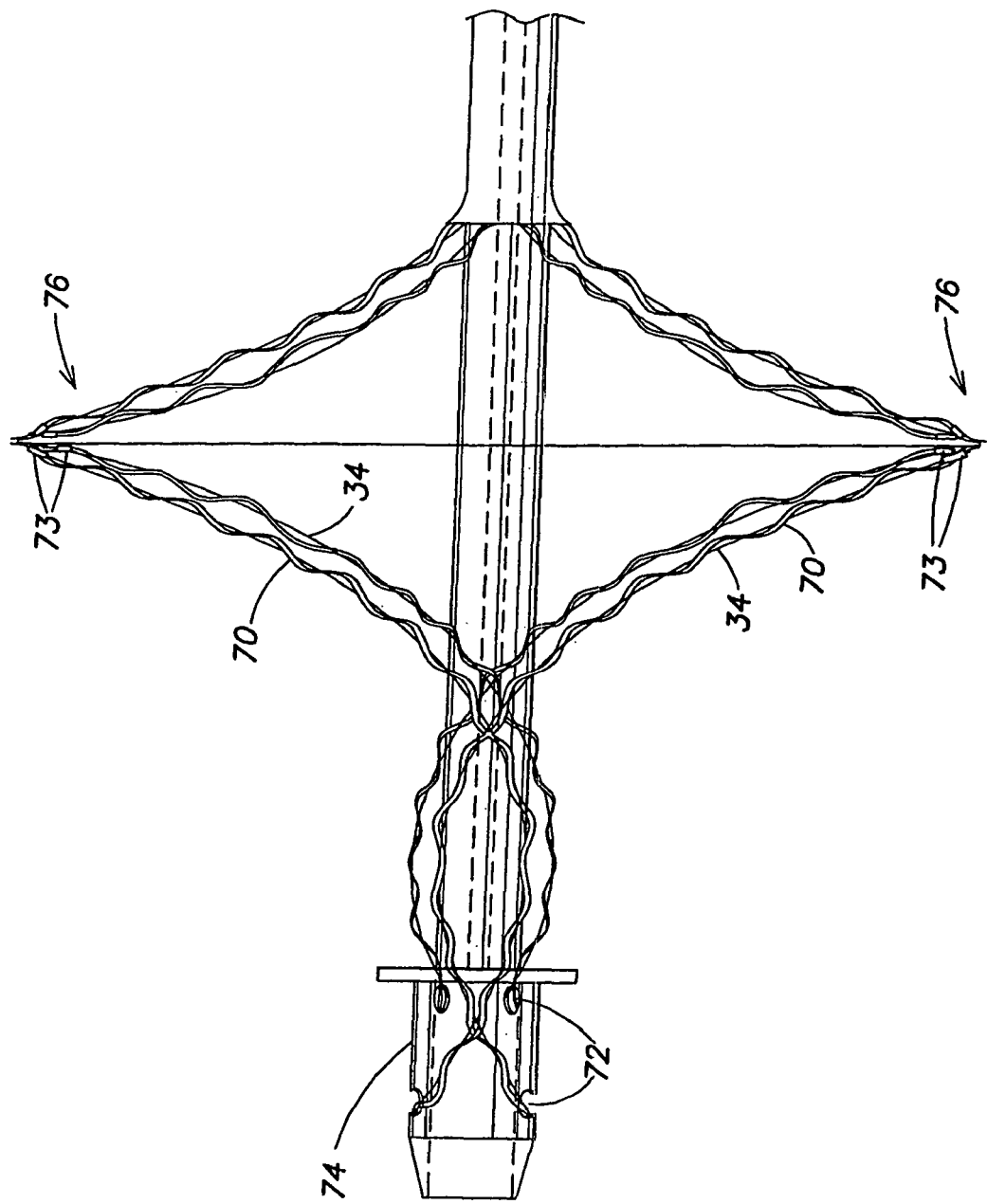

FIG. 10 illustrates a side view of braided conductive member 28 including temperature sensors 70. As shown in FIG. 10, temperature sensors 70 emerge from four holes 72. Each hole 72 is disposed in one quadrant of anchor 74. The temperature sensors 70 are bonded to the outside edge 76 of braided conductive member 28. Temperature sensors 70 may be isolated by a small piece of polyimide tubing 73 around them and then bonded in place to the filaments. The temperature sensors 7 may be woven and twisted into braided conductive member 28 or they can be bonded on a side-by-side or parallel manner with the filaments 34.

There are several methods of implementing electrically independent sectors. In one embodiment, the wires are preferably stripped of their insulative coating in the region forming the ablative ring (when expanded). However, sufficient insulation may be left on the wires in order to prevent interconnection when in the expanded state. Alternatively, adjacent mesh wires can be permitted to touch in their stripped region, but can be separated into groups by fully insulated (unstripped) wires imposed, for example, every 3 or 5 wires apart (the number of wires does not limit this invention), thus forming sectors of independently controllable zones. Each zone can have its own temperature sensor. The wires can be "bundled" (or independently attached) to independent outputs of an ablation energy generator. RF energy can then be titrated in its application to each zone by switching power on and off (and applying power to other zones during the 'off period') or by modulating voltage or current to the zone (in the case of independent controllers). In either case, the temperature inputs from the temperature sensors can be used in a standard feedback algorithm to control the power delivery.

Figure 10A:
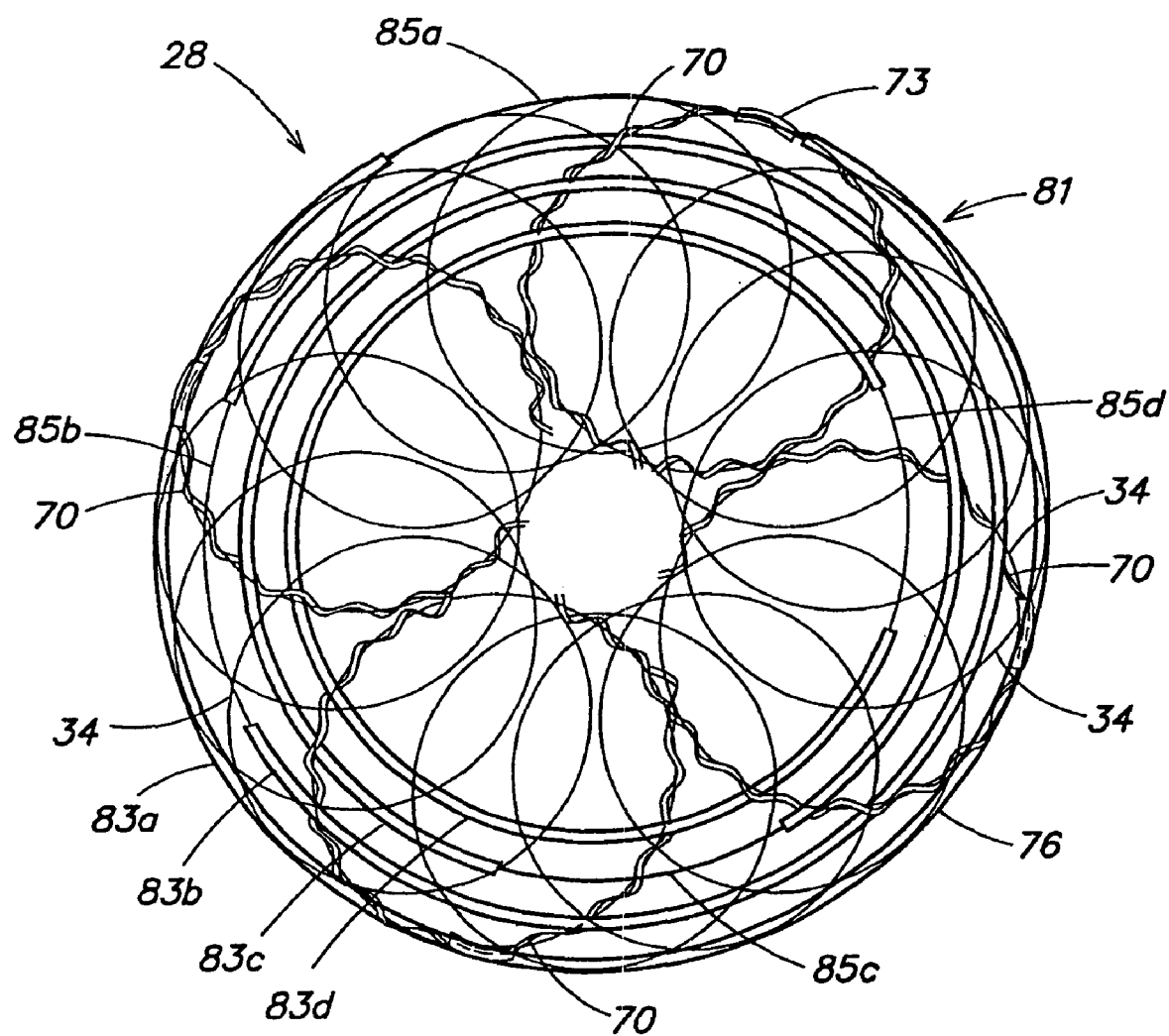

Alternatively, as illustrated in FIG. 10A, braided conductive member 28 may be used to support a ribbon-like structure which is separated into discrete sectors. As shown in FIG. 10A, the ribbon-like structure 81 may be, for example, a pleated copper flat wire that, as braided conductive member 28 expands, unfolds into an annular ring. Each of the wires 83*a*-83*d* lie in the same plane. Although four wires are illustrated in FIG. 10A, structure 81 may include any number of wires depending upon the application and desired performance. Each of wires 83*a*-83*d* is insulated. Insulation may then be removed from each wire to create different sectors 85*a*-85*d*. Alternatively, each of wires 83*a*-83*d* may be uninsulated and insulation may be added to create different sectors. The different sectors provide an ablative zone comprised of independently controllable wires 83*a*-83*d*. Temperature sensors 70 may be mounted on the individual wires, and filaments 34 may be connected to respective wires 83*a*-83*d* to provide independent control of energy to each individual sector. One skilled in the art will appreciate that each of wires 83*a*-83*d* can have multiple sectors formed by removing insulation in various locations and that numerous combinations of sectors 85*a*-85*d* and wires 83*a*-83*d* forming ribbon-like structure 81 can be obtained.

Further, according to the invention, some of sectors 85*a*-85*d* or wires 83*a*-83*d* may be used for mapping or electrical measurement, while other of these sectors 85*a*-85*d* or wires 83*a*-83*d* may be used for ablation. The mapping and ablations sectors and/or wires may be activated independently, and may be activated concurrently, if desired. One application of dedicating some sectors and/or wires for mapping and others for ablation is that a lesion may be formed and the quality of the lesion may be measured using a single braided conductive member 28. This can avoid the need to change catheters during a procedure. Thus, a single catheter may be used for both mapping and ablation.

The quality of a lesion may be determined by a measurement of the impedance of the ablated tissue or by a measurement of the electrical signal strength at the ablated tissue. Impedance of the tissue may be determined by measuring the resistance between any two sectors 85*a*-85*d* or wires 83*a*-83*d* dedicated to mapping based on a known input voltage or current. Ablated tissue has a higher impedance than healthy tissue; thus, a higher impedance value is indicative of a higher degree of ablation. Electrical signal strength may be a unipolar measurement based on a single sector 85*a*-85*d* or wire

83a-83d. If a measurement of a signal is detected in healthy tissue, the signal will have a higher amplitude than a signal that is detected in ablated tissue. Accordingly, a determination may be made as to the health of the tissue, or quality of the lesion.

Measurement of the impedance of the ablated tissue or measurement of the electrical signal strength at the ablated tissue, described above, may also be performed with other embodiments of the catheter 10 described herein. For example, in the embodiment of FIG. 8., one or more of the sixteen filaments 34 may be used to measure the signal strength of the ablated tissue. For example, a single filament 34 that is isolated from the other filaments or a group of electrically connected filaments may be used. Multiple measurements of the signal strength may be taken in different regions of the braided conductive member 28 and compared to assess the signal strength in different regions or quadrants of the braided conductive member 28. Similarly, any two of the sixteen filaments 34 of FIG. 8 or any two groups of electrically connected filaments, may be used to measure the signal strength of the ablated tissue to measure the impedance between each of the two filaments 34 or groups of filaments.

Either of the impedance measurement or the signal strength measurement may be performed independently by various sectors 85a-85d or wires 83a-83d of the braided conductive member. This allows an assessment of lesion quality to be performed for different regions of a lesion, corresponding to different quadrants of the braided conductive member 28.

Steering

Figure 13:
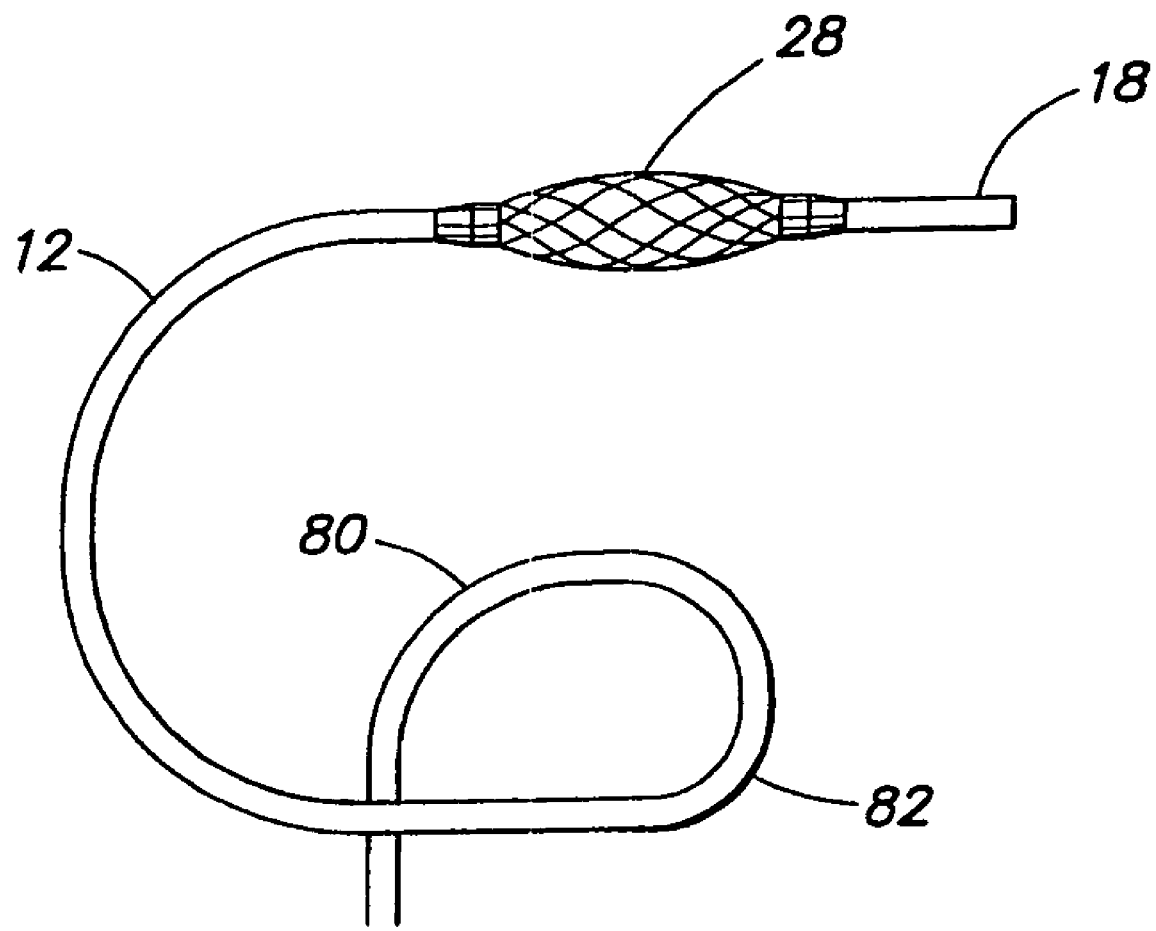

Reference is now made to FIGS. 11-13 which illustrate aspects of the steering capabilities of the present invention. As illustrated in FIGS. 1-2, catheter 10 is capable of being steered using control handle 14. In particular, FIG. 1 illustrates steering where the steering pivot or knuckle is disposed on catheter shaft 12 in a region that is distal to the braided conductive member 28.

FIG. 11 illustrates catheter 10 wherein the pivot point or steering knuckle is disposed proximal to braided conductive member 28.

FIG. 12 illustrates catheter 10 having the capability of providing steering knuckles both proximal and distal to braided conductive member 28.

FIGS. 1-2, and 11-12 illustrate two dimensional or single plane type steering. The catheter of the present invention can also be used in connection with a three dimensional steering mechanism. For example, using the control handle in the incorporated by reference '852 patent, the catheter can be manipulated into a three-dimensional "lasso-like" shape, particularly at the distal end of the catheter. As shown in FIG. 13, the catheter can have a primary curve 80 in one plane and then a second curve 82 in another plane at an angle to the first plane. With this configuration, the catheter can provide increased access to difficult to reach anatomical structures. For example, a target site for a mapping or ablation operation may be internal to a blood vessel. Thus, the increased steering capability can allow easier access into the target blood vessel. In addition, the additional dimension of steering can allow for better placement of braided conductive member 28 during an ablation or mapping procedure. Catheter 10 can be inserted into a site using the steering capabilities provided by primary curve 80. Thereafter, using the secondary curve 82, braided conductive member 28 can be tilted into another plane for better orientation or contact with the target site.

Conductive Member Configurations and Materials

Reference is now made to FIGS. 14-17 which figures illustrate other configurations of braided conductive member 28. As has been described above and will be described in more detail, braided conductive member 28 can include from one to 300 or more filaments. The filaments may vary from very fine wires having small diameters or cross-sectional areas to large wires having relatively large diameters or cross-sectional areas.

Figure 14:
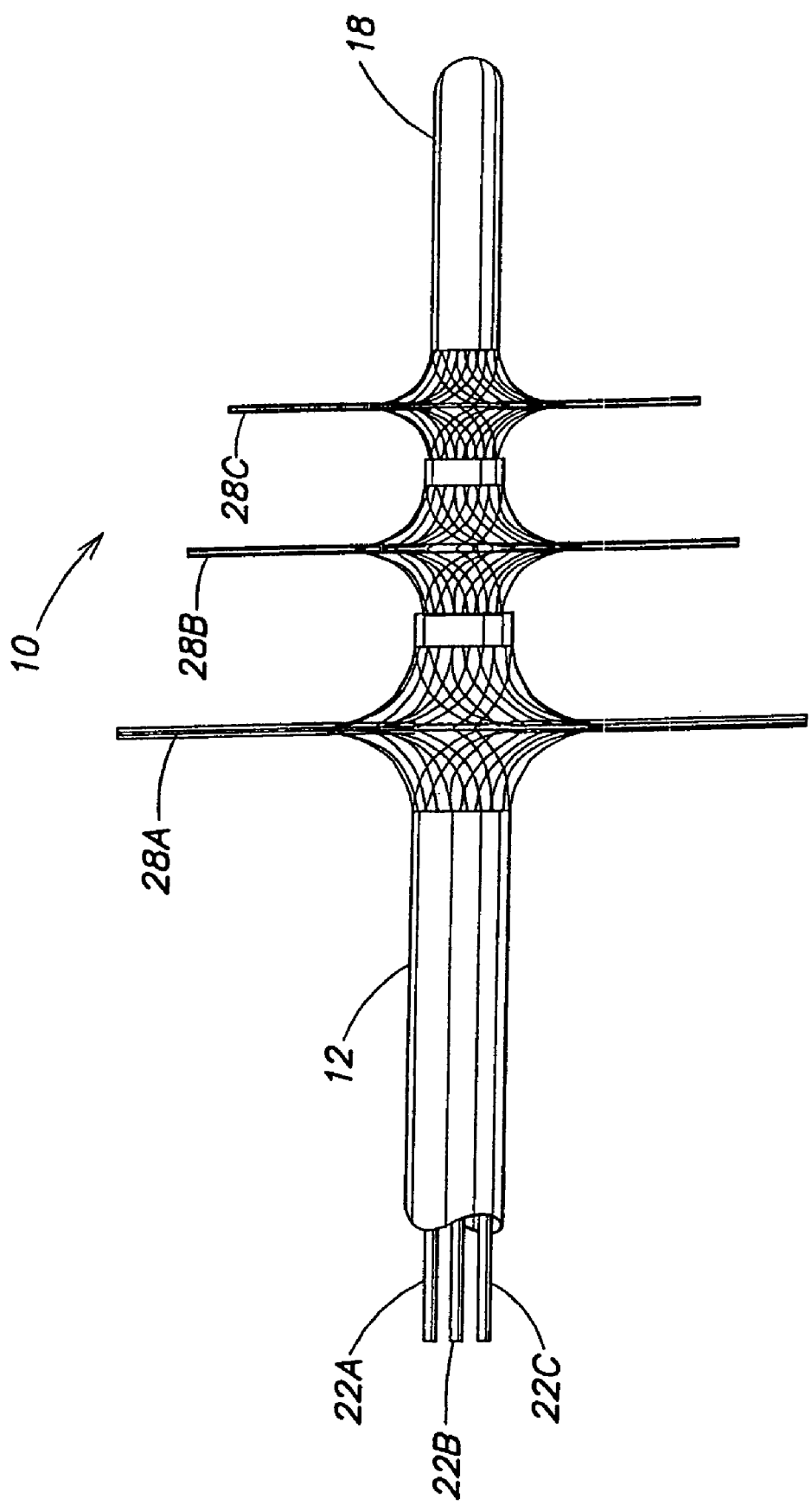
FIGS. 14-17 illustrate further embodiments of the braided conductive member.

FIG. 14 illustrates the use of more than one braided conductive member 28 as the distal end of catheter 10. As shown in FIG. 14, three braided conductive members 28A, 28B, and 28C are provided at the distal end of catheter 10. Braided conductive members 28A, 28B, and 29C may be, in their expanded conditions, the same size or different sizes. Each of the braided conductive members 28A, 28B, and 28C can be expanded or contracted independently in the manner illustrated in FIGS. 1-4 via independent control shafts 26A, 26B, and 26C. The use of multiple braided conductive members provides several advantages. Rather than having to estimate or guess as to the size of the blood vessel prior to starting a mapping or ablation procedure, if braided conductive members 28A, 28B, and 28C are of different expanded diameters, than sizing can be done in vivo during a procedure. In addition, one of the braided conductive members can be used for ablation and another of the braided conductive members can be used for mapping. This allows for quickly checking the effectiveness of an ablation procedure.

Figure 15A:
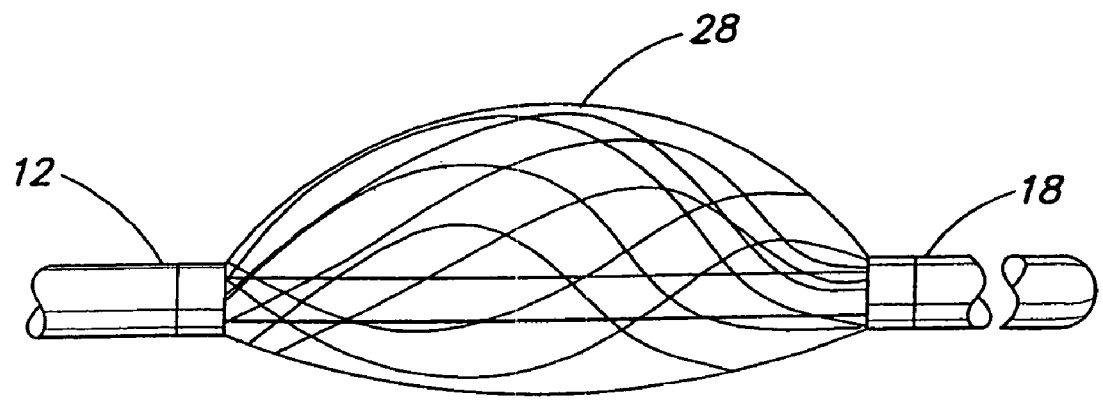
Figure 15B:
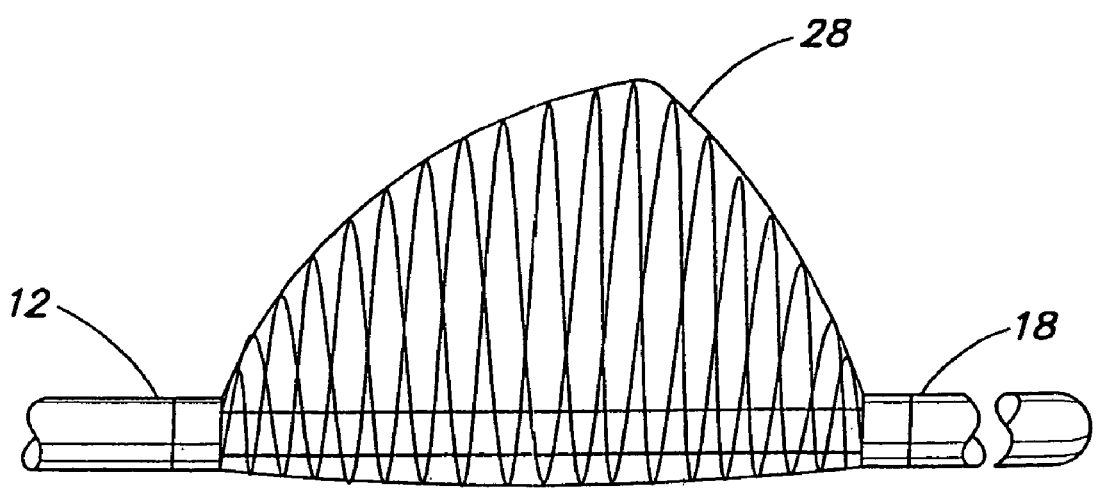

Reference is now made to FIGS. 15A and 15B, which figures illustrate other shapes of braided conductive member 28. As described up to this point, braided conductive member 28 is generally symmetrical and coaxial with respect to catheter shaft 12. However, certain anatomical structures may have complex three-dimensional shapes that are not easily approximated by a geometrically symmetrical mapping or ablation structure. One example of this type of structure occurs at the CS ostium. To successfully contact these types of anatomical structures, braided conductive member 28 can be "preformed" to a close approximation of that anatomy, and yet still be flexible enough to adapt to variations found in specific patients. Alternatively, braided conductive member 28 can be "preformed" to a close approximation of that anatomy, and be of sufficient strength (as by choice of materials, configuration, etc.) to force the tissue to conform to variations found in specific patients. For example FIG. 15A illustrates braided conductive member 28 disposed about shaft 12 in an off-center or non concentric manner. In addition, braided conductive member 28 may also be constructed so that the parameter of the braided conductive member in its expanded configuration has a non-circular edge so as to improve tissue contact around the parameter of the braided conductive member. FIG. 15B illustrates an example of this type of configuration where the braided conductive member 28 is both off center or non concentric with respect to catheter shaft 12 and also, in its deployed or expanded configuration, has an asymmetric shape. The eccentricity of braided conductive member 28 with respect to the shaft and the asymmetric deployed configurations can be produced by providing additional structural supports in braided conductive member 28, for example, such as by adding nitinol, ribbon wire, and so on. In addition, varying the winding pitch or individual filament size or placement or deforming selective filaments in braided conductive member 28 or any other means known to those skilled in the art may be used.

Figure 16A:
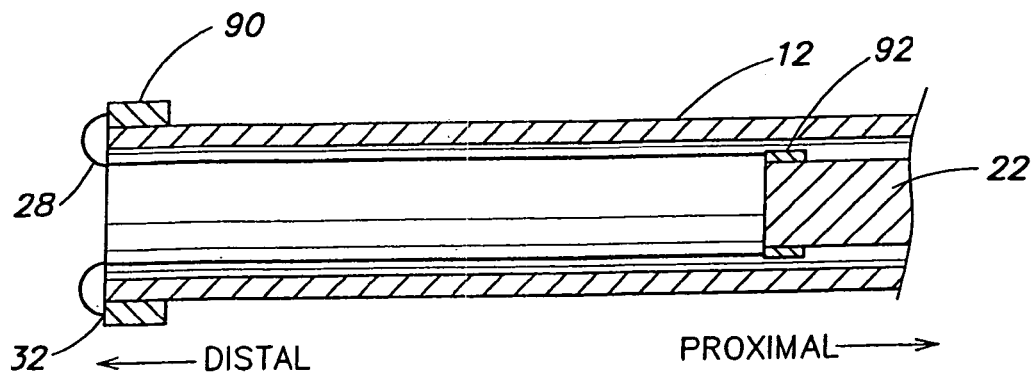
Figure 16B:
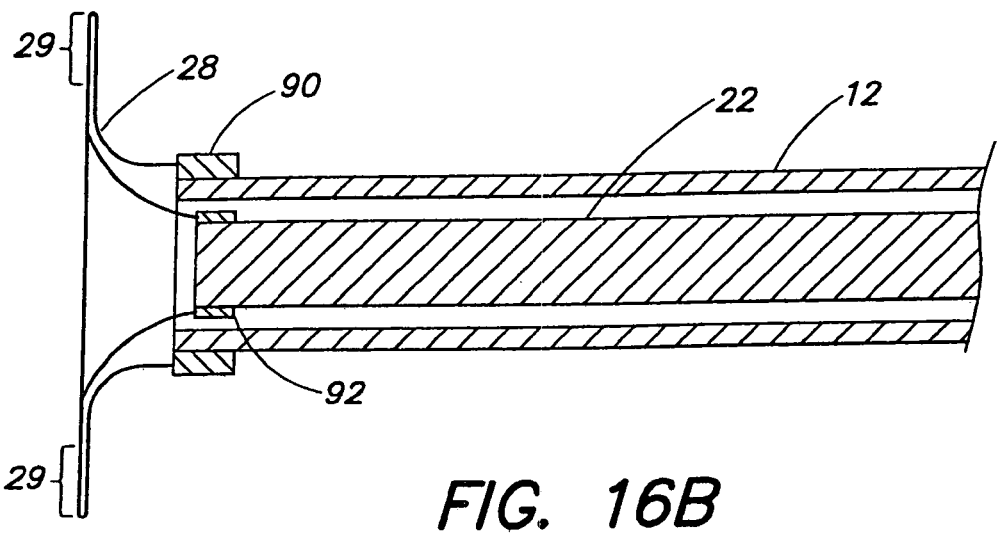
Figure 16C:
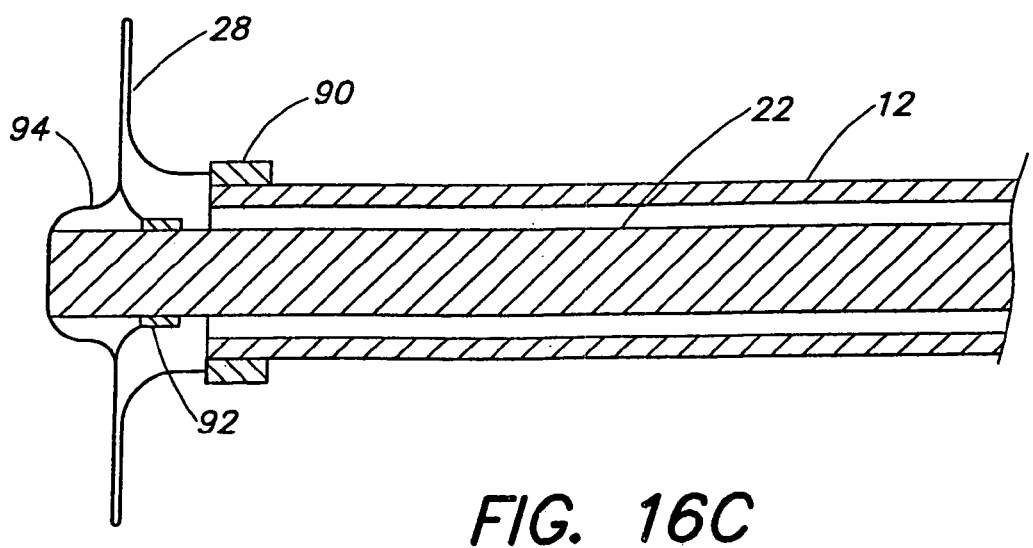

FIGS. 16A-16C illustrate another configuration of braided conductive member 28 and catheter 10. As illustrated in FIGS. 16A-16C, the distal tip section of catheter 10 has been removed and braided conductive member 28 is disposed at the distal end of catheter 10. One end of braided conductive member 28 is anchored to catheter shaft 12 using an anchor band 90 that clamps the end 32 of braided conductive member 28 to catheter shaft 12. The other end of braided conductive member 28 is clamped to an activating shaft such as shaft 26 using another anchor band 92. FIG. 16A illustrates braided conductive member 28 in its undeployed configuration. As shaft 26 is moved distally, braided conductive member 28 emerges or everts from shaft 12. As shown in FIG. 16B, braided conductive member 28 has reached its fully deployed diameter and an annular tissue contact zone 29 can be placed against an ostium or other anatomical structure. As illustrated in FIG. 16C, further distal movement of shaft 26 can be used to create a concentric locating region 94 that can help to provide for concentric placement within an ostium of a pulmonary vein, for example. Concentric locating region 94 may be formed by selective variations in the winding density of filaments 34 in braided conductive member 28, preferential predeformation of the filaments, additional eversion of braided conductive member 28 from shaft 12, or by other means known to those skilled in the art.

Figure 17:
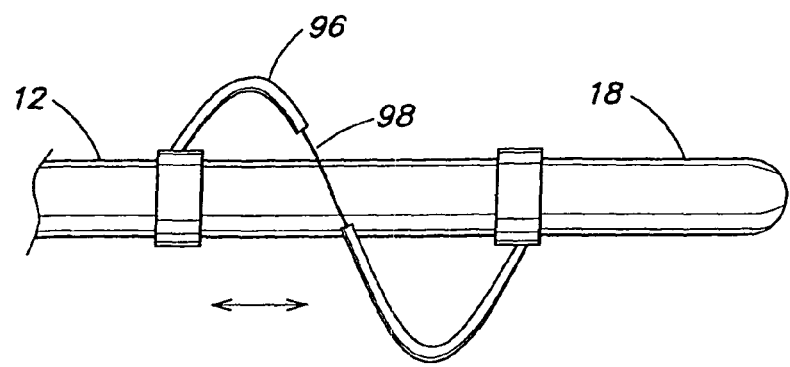

Reference is now made to FIG. 17, which figure illustrates a further embodiment of braided conductive member 28. As illustrated in FIG. 17, braided conductive member 28 is composed of one or several large wires 96 rather than a multiplicity of smaller diameter wires. The wire or wires can be moved between the expanded and unexpanded positions in the same manner as illustrated in FIG. 1. In addition, a region 98 may be provided in which the insulation has been removed for mapping or ablation procedures. The single wire or "corkscrew" configuration provides several advantages. First, the wire or wires do not cross each other and therefore there is only a single winding direction required for manufacture. In addition, the risk of thrombogenicity may be reduced because there is a smaller area of the blood vessel being blocked. In addition, the connections between the ends of the large wire and the control shafts may be simplified.

The catheter 10 of the present invention can be coated with a number of coatings that can enhance the operating properties of braided conductive member 28. The coatings can be applied by any of a number of techniques and the coatings may include a wide range of polymers and other materials.

Braided conductive member 28 can be coated to reduce its coefficient of friction, thus reducing the possibility of thrombi adhesion to the braided conductive member as well as the possibility of vascular or atrial damage. These coatings can be combined with the insulation on the filaments that make up braided conductive member 28, these coatings can be included in the insulation itself, or the coatings can be applied on top of the insulation. Examples of coating materials that can be used to improve the lubricity of the catheter include PD slick available from Phelps Dodge Corporation, Ag, Tin, BN. These materials can be applied by an ion beam assisted deposition ("IBAD") technique developed by, for example, Amp Corporation.

Braided conductive member 28 can also be coated to increase or decrease its thermal conduction which can improve the safety or efficacy of the braided conductive member 28. This may be achieved by incorporating thermally conductive elements into the electrical insulation of the filaments that make up braided conductive member 28 or as an added coating to the assembly. Alternatively, thermally insulating elements may be incorporated into the electrical insulation of the filaments that make up braided conductive member 28 or added as a coating to the assembly. Polymer mixing, IBAD, or similar technology could be used to add Ag, Pt, Pd, Au, Ir, Cobalt, and others into the insulation or to coat braided conductive member 28.

Radioopaque coatings or markers can also be used to provide a reference point for orientation of braided conductive member 28 when viewed during fluoroscopic imaging. The materials that provide radiopacity including, for example, Au, Pt, Ir, and other known to those skilled in the art. These materials may be incorporated and used as coatings as described above.

Antithrombogenic coatings, such as heparin and BH, can also be applied to braided conductive member 28 to reduce thrombogenicity to prevent blood aggregation on braided conductive member 28. These coatings can be applied by dipping or spraying, for example.

As noted above, the filament 34 of braided conductive member 28 may be constructed of metal wire materials. These materials may be, for example, MP35N, nitinol, or stainless steel. Filaments 34 may also be composites of these materials in combination with a core of another material such as silver or platinum. The combination of a highly conductive electrical core material with another material forming the shell of the wire allows the mechanical properties of the shell material to be combined with the electrical conductivity of the core material to achieve better and/or selectable performance. The choice and percentage of core material used in combination with the choice and percentage of shell material used can be selected based on the desired performance characteristics and mechanical/electrical properties desired for a particular application.

Irrigation

Figure 18:
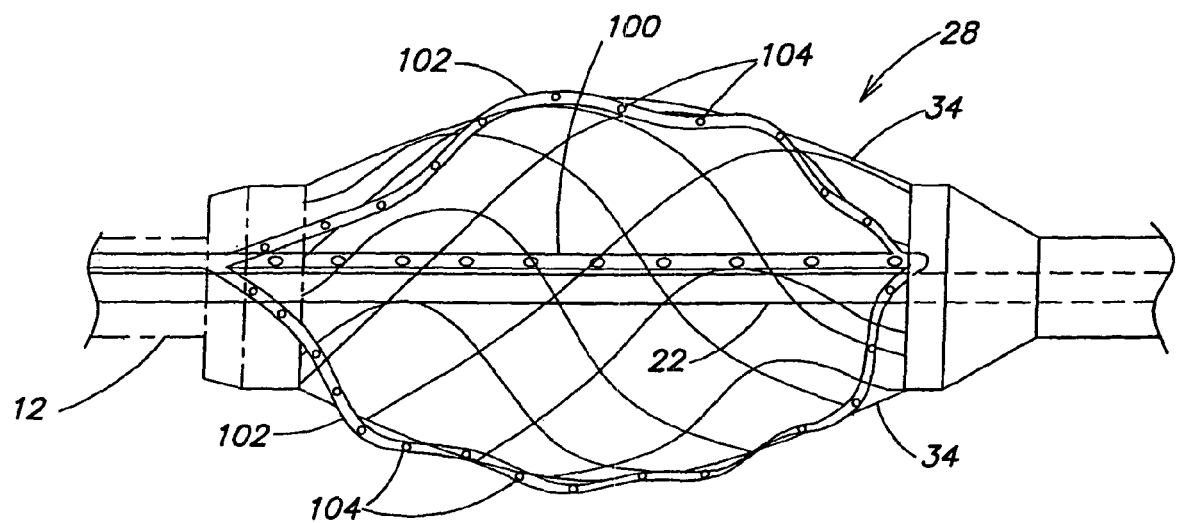
FIGS. 18-19A illustrate the use of irrigation in connection with the present invention.

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches a 100° C. One way of maintaining the temperature less than or equal to this limit is to irrigate the ablation electrode with saline to provide convective cooling so as to control the electrode-tissue interface temperature and thereby prevent an increase in impedance. Accordingly, irrigation of braided conductive member 28 and the tissue site at which a lesion is to be created can be provided in the present invention. FIG. 18 illustrates the use of an irrigation manifold within braided conductive member 28. An irrigation manifold 100 is disposed along shaft 22 inside braided conductive member 28. Irrigation manifold 100 may be one or more polyimid tubes. Within braided conductive member 28, the irrigation manifold splits into a number of smaller tubes 102 that are woven into braided conductive member 28 along a respective filament 34. A series of holes 104 may be provided in each of the tubes 102. These holes can be oriented in any number of ways to target a specific site or portion of braided conductive member 28 for irrigation. Irrigation manifold 100 runs through catheter shaft 12 and may be connected to an irrigation delivery device outside the patient used to inject an irrigation fluid, such as saline, for example, such as during an ablation procedure.

The irrigation system can also be used to deliver a contrast fluid for verifying location or changes in vessel diameter. For example, a contrast medium may be perfused prior to ablation and then after an ablation procedure to verify that there have been no changes in the blood vessel diameter. The contrast medium can also be used during mapping procedures to verify placement of braided conductive member 28. In either ablation or mapping procedures, antithrombogenic fluids, such as heparin can also be perfused to reduce thrombogenicity.

Figure 19:
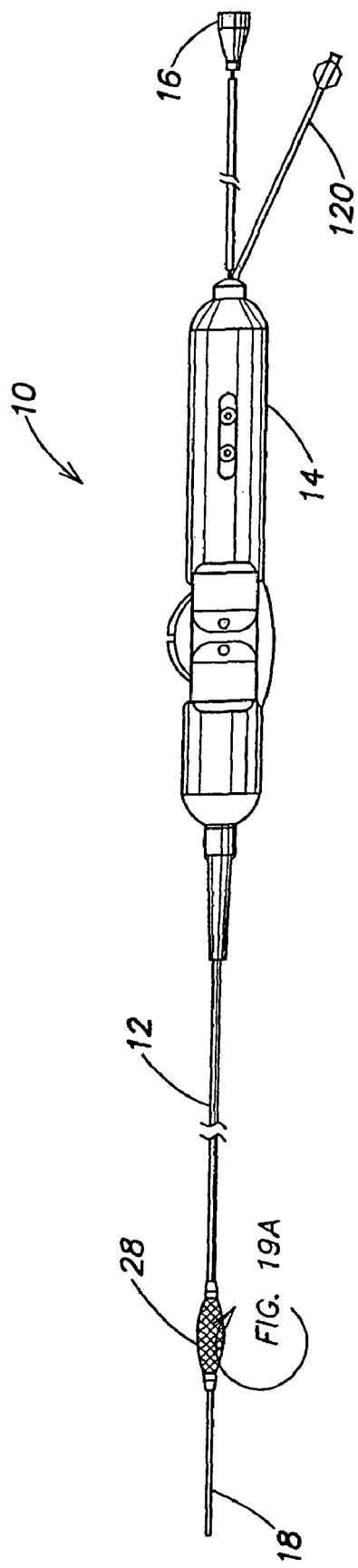
Figure 19A:
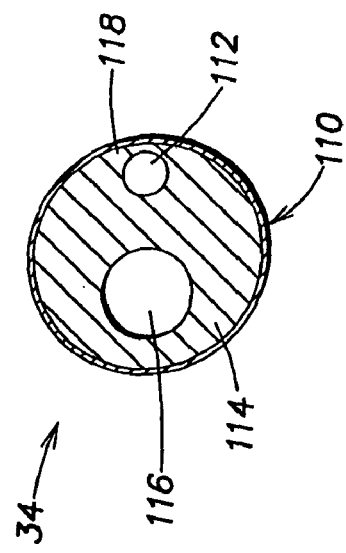

FIG. 19 illustrates another way of providing perfusion/irrigation in catheter 10. As illustrated in FIG. 19, the filaments 34 that comprise braided conductive member 28 are composed of a composite wire 110. The composite wire 110 includes an electrically conductive wire 112 that is used for delivering ablation energy in an ablation procedure or for detecting electrical activity during a mapping procedure. Electrical wire 112 is contained within a lumen 114 that also contains a perfusion lumen 116. Perfusion lumen 116 is used to deliver irrigation fluid or a contrast fluid as described in connection with FIG. 18. Once braided conductive member 28 has been constructed with composite wire 110, the insulation 118 surrounding wire filament 112 can be stripped away to form an electrode surface. Holes can then be provided into perfusion lumen 116 to then allow perfusion at targeted sites along the electrode surface. As with the embodiment illustrated in FIG. 18, the perfusion lumens can be connected together to form a manifold which manifold can then be connected to, for example, perfusion tube 120 and connected to a fluid delivery device.

Shrouds

The use of a shroud or shrouds to cover at least a portion of braided conductive member 28 can be beneficial in several ways. The shroud can add protection to braided conductive member 28 during insertion and removal of catheter 10. A shroud can also be used to form or shape braided conductive member 28 when in its deployed state. Shrouds may also reduce the risk of thrombi formation on braided conductive member 28 by reducing the area of filament and the number of filament crossings exposed to blood contact. This can be particularly beneficial at the ends 30 and 32 of braided conductive member 28. The density of filaments at ends 30 and 32 is greatest and the ends can therefore be prone to blood aggregation. The shrouds can be composed of latex balloon material or any material that would be resistant to thrombi formation durable enough to survive insertion through an introducer system, and would not reduce the mobility of braided conductive member 28. The shrouds can also be composed of an RF transparent material that would allow RF energy to pass through the shroud. If an RF transparent material is used, complete encapsulation of braided conductive member 28 is possible.

A shroud or shrouds may also be useful when irrigation or perfusion is used, since the shrouds can act to direct irrigation or contrast fluid to a target region.

Figure 20A:
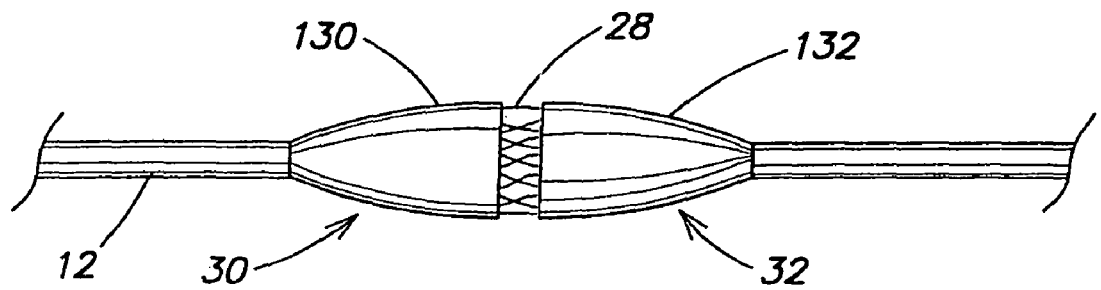
FIGS. 20A-20E illustrate the use of shrouds in the present invention.
Figure 20B:
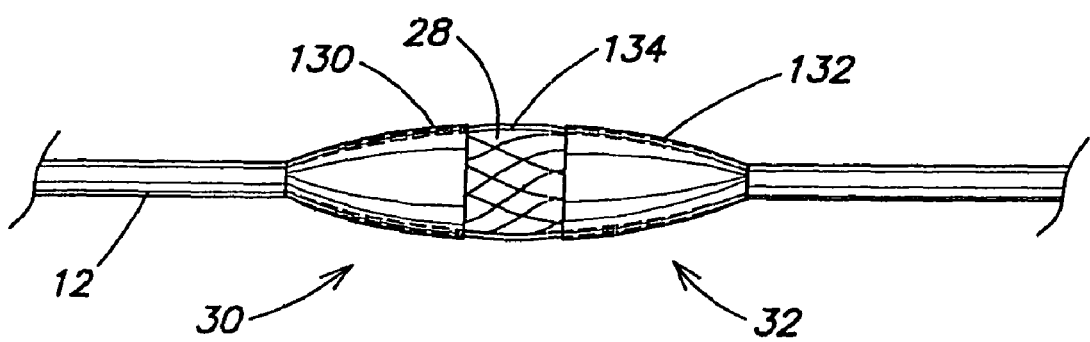

FIGS. 20A-20E illustrate various examples of shrouds that may be used in the present invention. FIG. 20A illustrates shrouds 130 and 132 disposed over end regions 31 and 33, respectively, of braided conductive member 28. This configuration can be useful in preventing coagulation of blood at the ends of braided conductive member 28. FIG. 20B illustrates shrouds 130 and 132 used in conjunction with an internal shroud 134 contained inside braided conductive member 28. In addition to preventing blood coagulation in regions 31 and 32, the embodiment illustrated in FIG. 20B also prevents blood from entering braided conductive member 28.

Figure 20C:
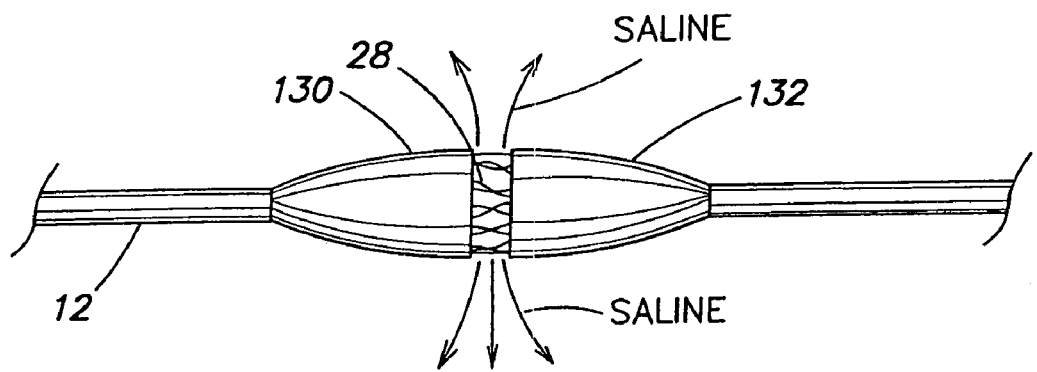

FIG. 20C illustrates shrouds 130 and 132 being used to direct and irrigation fluid or contrast medium along the circumferential edge of braided conductive member 28. In the embodiment illustrated in FIG. 20C, perfusion can be provided as illustrated in FIGS. 18 and 19.

Figure 20D:
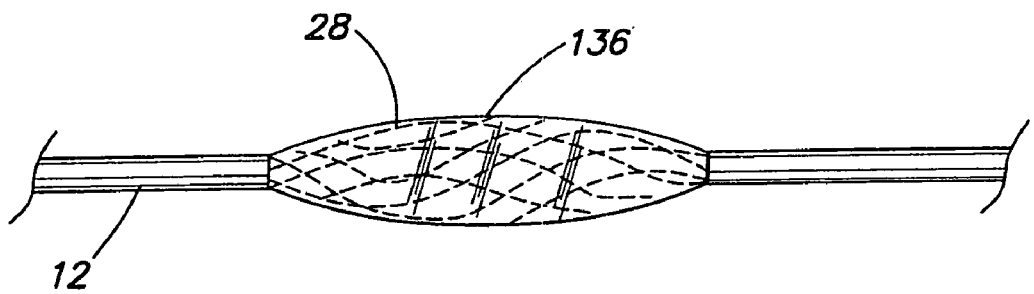

FIG. 20D illustrates the use of an external shroud that covers braided conductive member 28. Shroud 136 completely encases braided conductive member 28 and thereby eliminates blood contact with braided conductive member 28. Shroud 136 may be constructed of a flexible yet ablation-energy transparent material so that, when used in an ablation procedure, braided conductive member 28 can still deliver energy to a targeted ablation site.

Figure 20E:
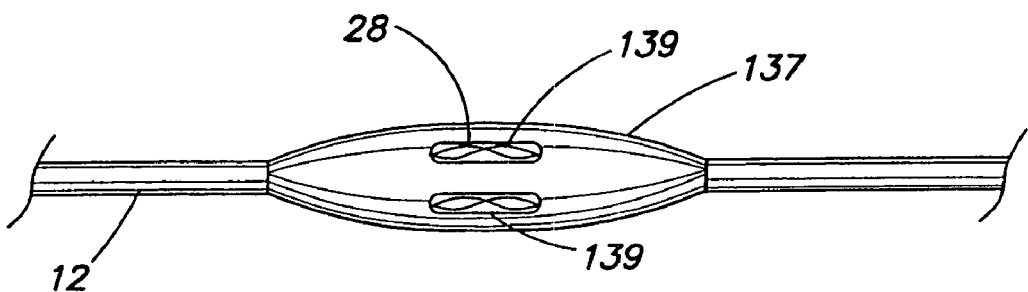

FIG. 20E also illustrates an external shroud 137 encasing braided conductive member 28. Shroud 137 may also be constructed of a flexible yet ablation-energy transparent material. Openings 139 may be provided in shroud 137 to allow the portions of braided conductive member 28 that are exposed by the opening to come into contact with tissue. Openings 139 may be elliptical, circular, circumferential, etc.

Guiding Sheaths

There may be times during ablation or mapping procedures when catheter 10 is passing through difficult or tortuous vasculature. During these times, it may be helpful to have a guiding sheath through which to pass catheter 10 so as to allow easier passage through the patient's vasculature.

Figure 21:
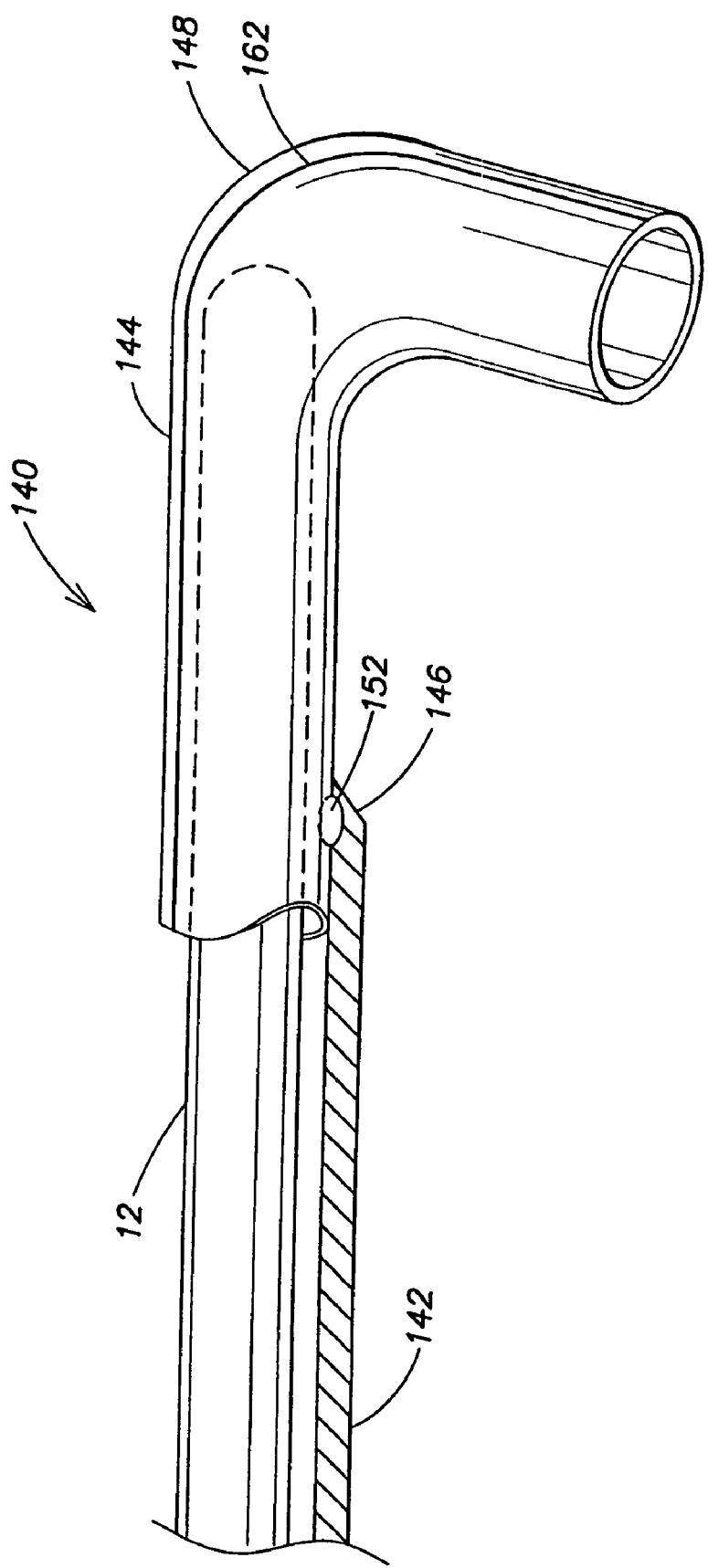
FIG. 21 illustrates a guiding sheath that may be used in connection with the present invention.

FIG. 21 illustrates one example of a guiding sheath that may be used in connection with catheter 10. As illustrated in FIG. 21, the guiding sheath 140 includes a longitudinal member 142. Longitudinal member 142 may be constructed of a material rigid enough to be pushed next to catheter shaft 12 as the catheter is threaded through the vasculature. In one example, longitudinal member 142 may be stainless steel. Longitudinal member 142 is attached to a sheath 144 disposed at the distal end 146 of longitudinal member 142. The split sheath 144 may have one or more predetermined curves 148 that are compatible with the shapes of particular blood vessels (arteries or veins) that catheter 10 needs to pass through. Split sheath 144 may extend proximally along longitudinal member 142. For example, sheath 144 and longitudinal member 142 may be bonded together for a length of up to 20 or 30 centimeters to allow easier passage through the patient's blood vessels. Sheath 144 includes a predetermined region that extends longitudinally along sheath 144. Region may be, for example, a seam, that allows sheath 144 to be split open so that the guiding sheath 140 can be pulled back and peeled off catheter shaft 12 in order to remove the sheath.

In another embodiment, longitudinal member 142 may be a hypotube or the like having an opening 152 at distal end 146 that communicates with the interior of sheath 144. In this embodiment, longitudinal member 142 can be used to inject irrigation fluid such as saline or a contrast medium for purposes of cooling, flushing, or visualization.

Localization

Localization refers to a number of techniques whereby the location of catheter 1 in a patient can be determined. Apparatus and methods for localization can be incorporated into catheter 10.

An electromagnetic sensor, used for localization, may be fixed within the shaft of the catheter 10 using any suitable mechanism, such as glue or solder. The electromagnetic sensor generates signals indicative of the location of the electromagnetic sensor. A wire electrically connects the electromagnetic sensor to the controller 8, allowing the generated signals to be transmitted to the controller 8 for processing.

In addition to the electromagnetic sensor fixed to the catheter, a second electromagnetic sensor is provided that is fixed relative to the patient. The second electromagnetic sensor is attached, for example, to the patient's body, and serves as a reference sensor. A magnetic field is also provided, which is exposed to the electromagnetic sensors. Coils within each electromagnetic sensor generate electrical currents when exposed to the magnetic field. The electrical current generated by the coils of each sensor corresponds to a position of each sensor within the magnetic field. Signals generated by the reference electromagnetic sensor and electromagnetic sensor fixed to the catheter are analyzed by the controller 8 to ascertain a precise location of electromagnetic sensor fixed to the catheter 10.

Further, the signals can be used to generate a contour map of the heart. The map may be generated by contacting the catheter 10 with the heart tissue at a number of locations along the heart wall. At each location, the electric signals generated by the electromagnetic sensors are transmitted to the controller 8, or to another processor, to determine and record a location of the catheter 10. The contour map is generated by compiling the location information for each point of contact. This map may be correlated with heart signal data, measured by one or more electrodes on the catheter, for each location to generate a map of both the shape and electrical activity of the heart. Signals generated by the electromagnetic sensors may also be analyzed to determine a displacement of the catheter 10 caused by heartbeat.

As an alternative to the use of electromagnetic sensors other conventional techniques, such as ultrasound or magnetic resonance imaging (MRI) can also be used for localization of catheter 10.

In addition, an impedance-based sensor can also be incorporated into catheter 10. In an impedance-based system, several, such as three, high frequency signals are generated along different axes. The catheter electrodes may be used to sense these frequencies, and with appropriate filtering, the strength of the signal and thus the position of the catheter can be determined.

Methods of Use

Figure 22:
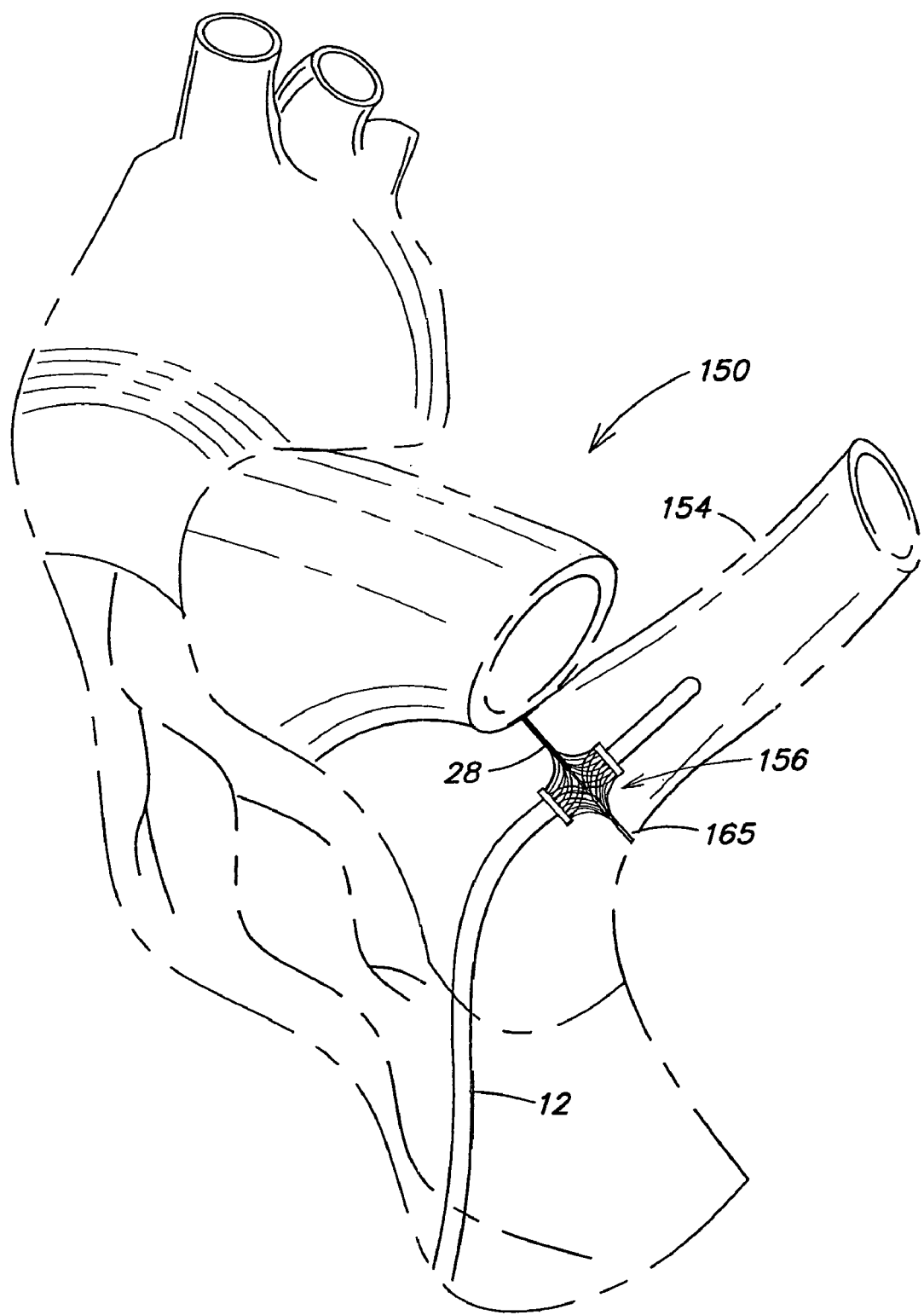
FIGS. 22-24 illustrate methods of using the present invention.
Figure 23:
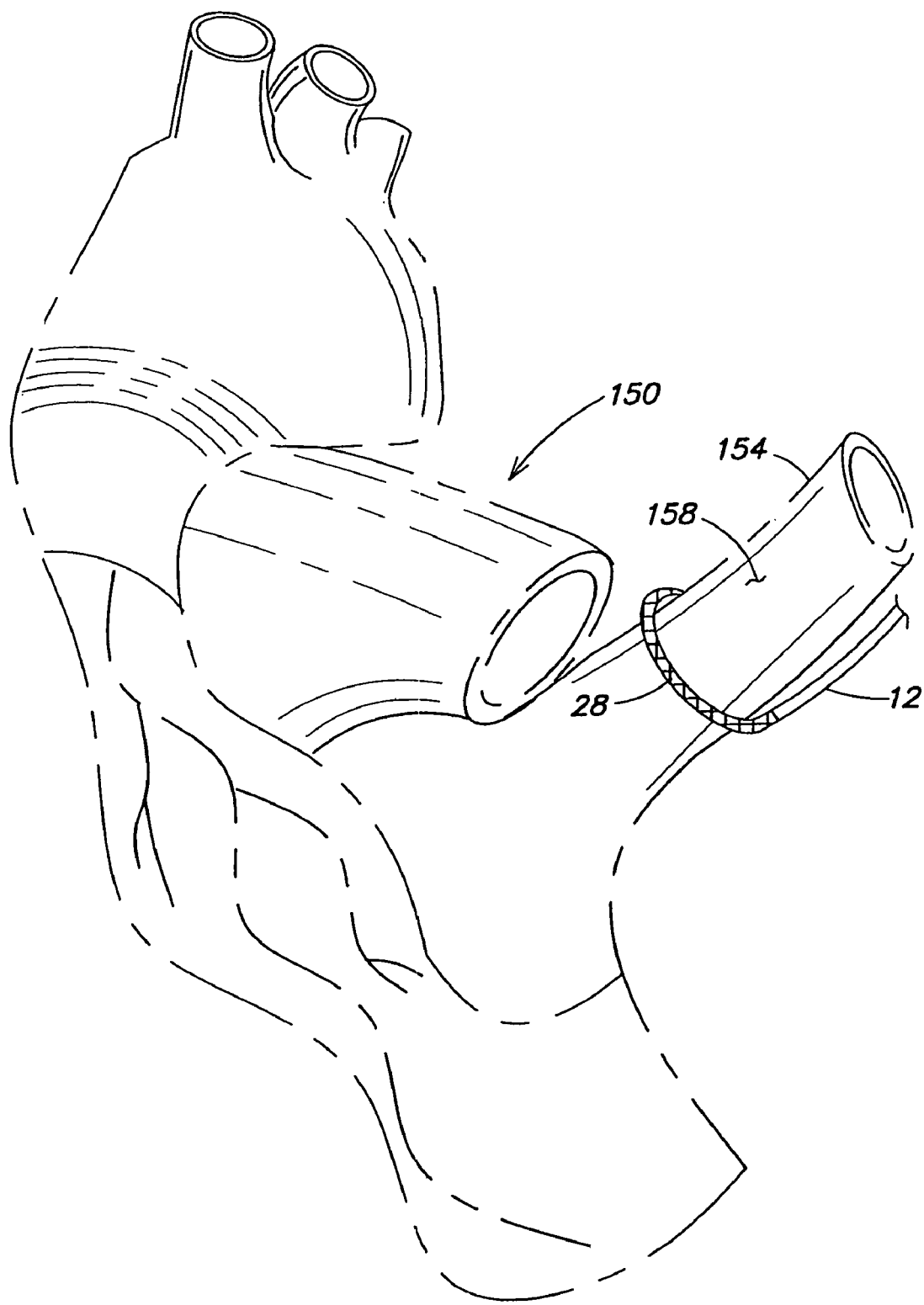
Figure 24:
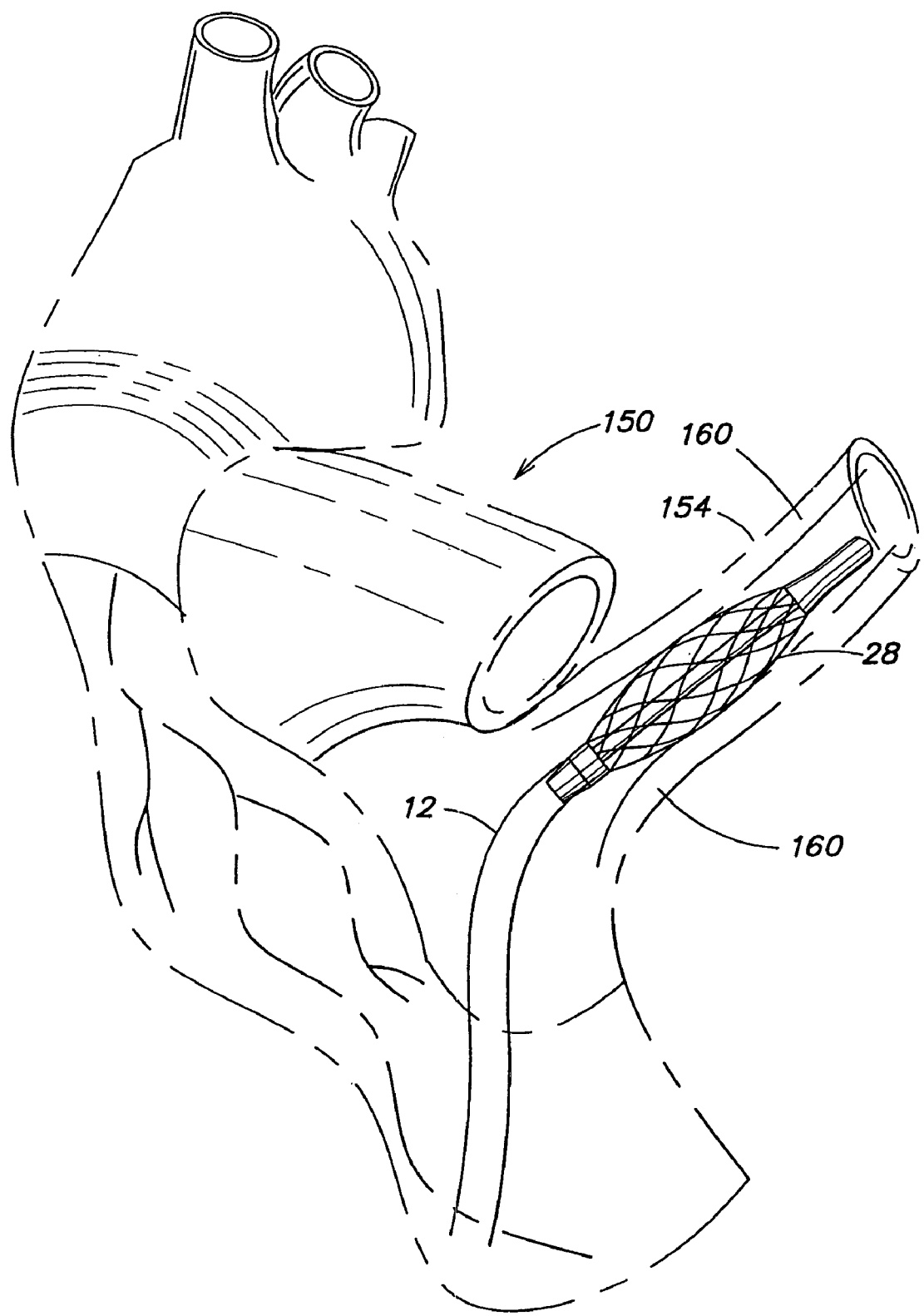
Figure 25A:
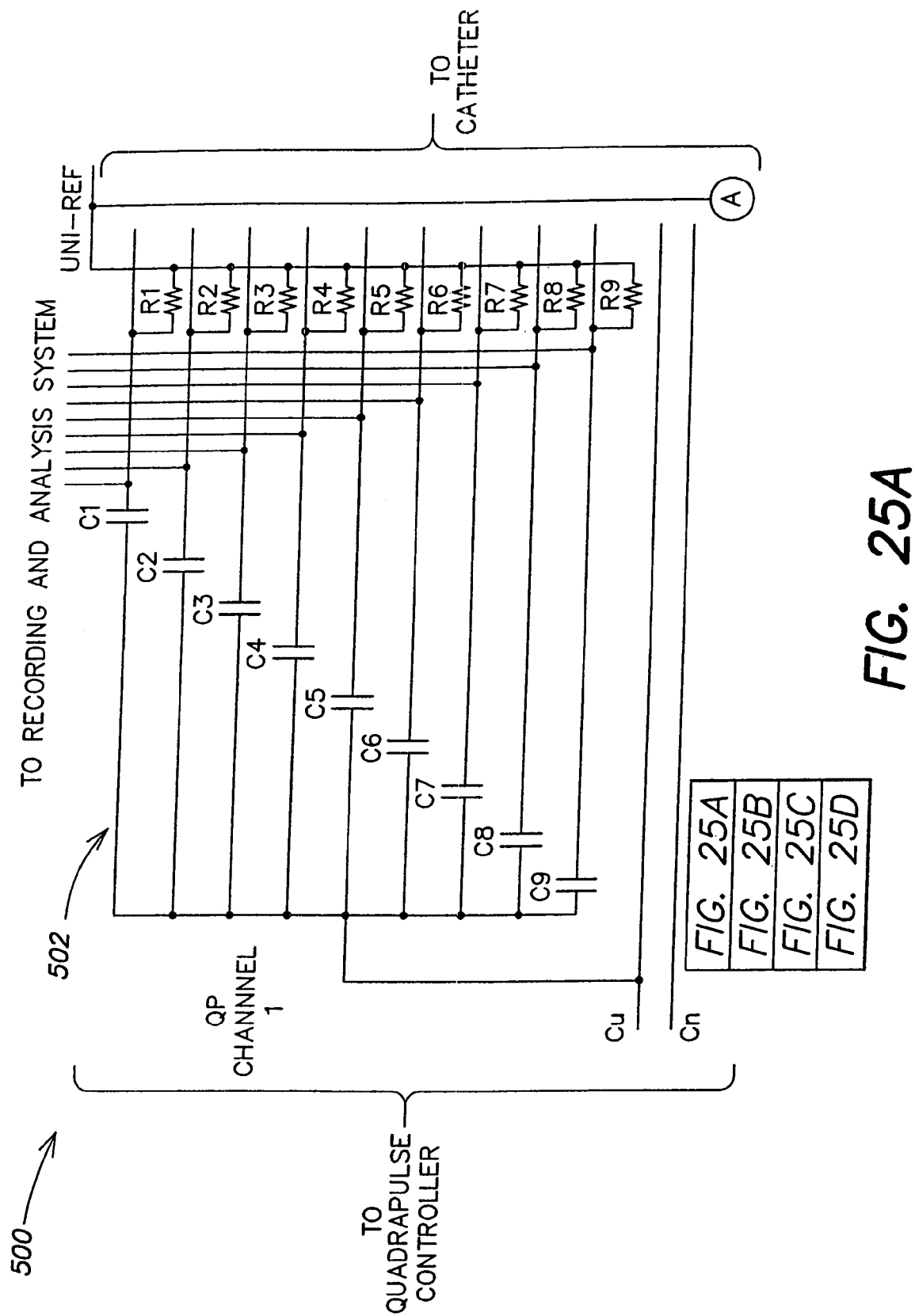
FIGS. 25A-25D illustrate control circuitry that may be used in connection with the controller.
Figure 25B:
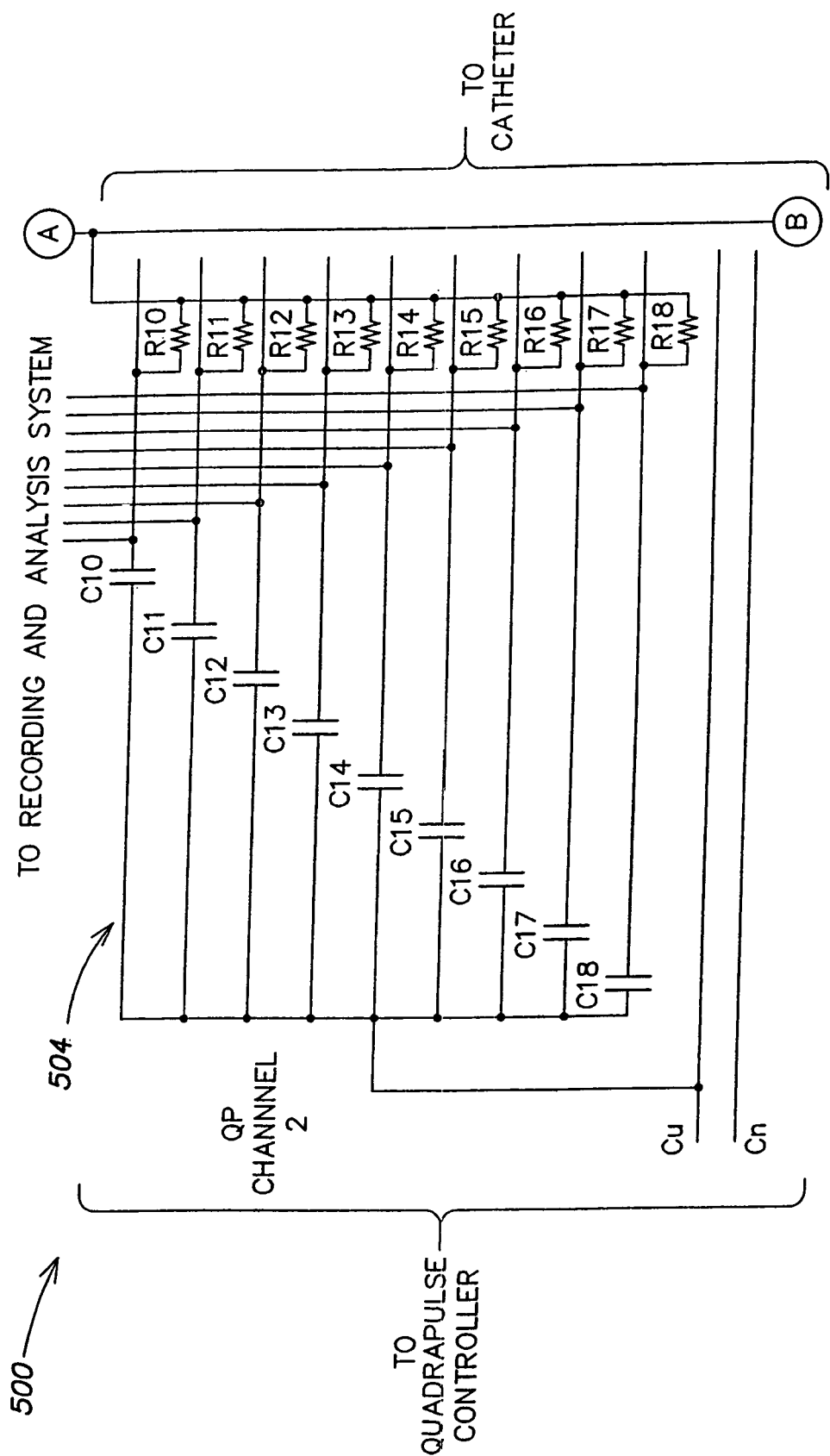
Figure 25C:
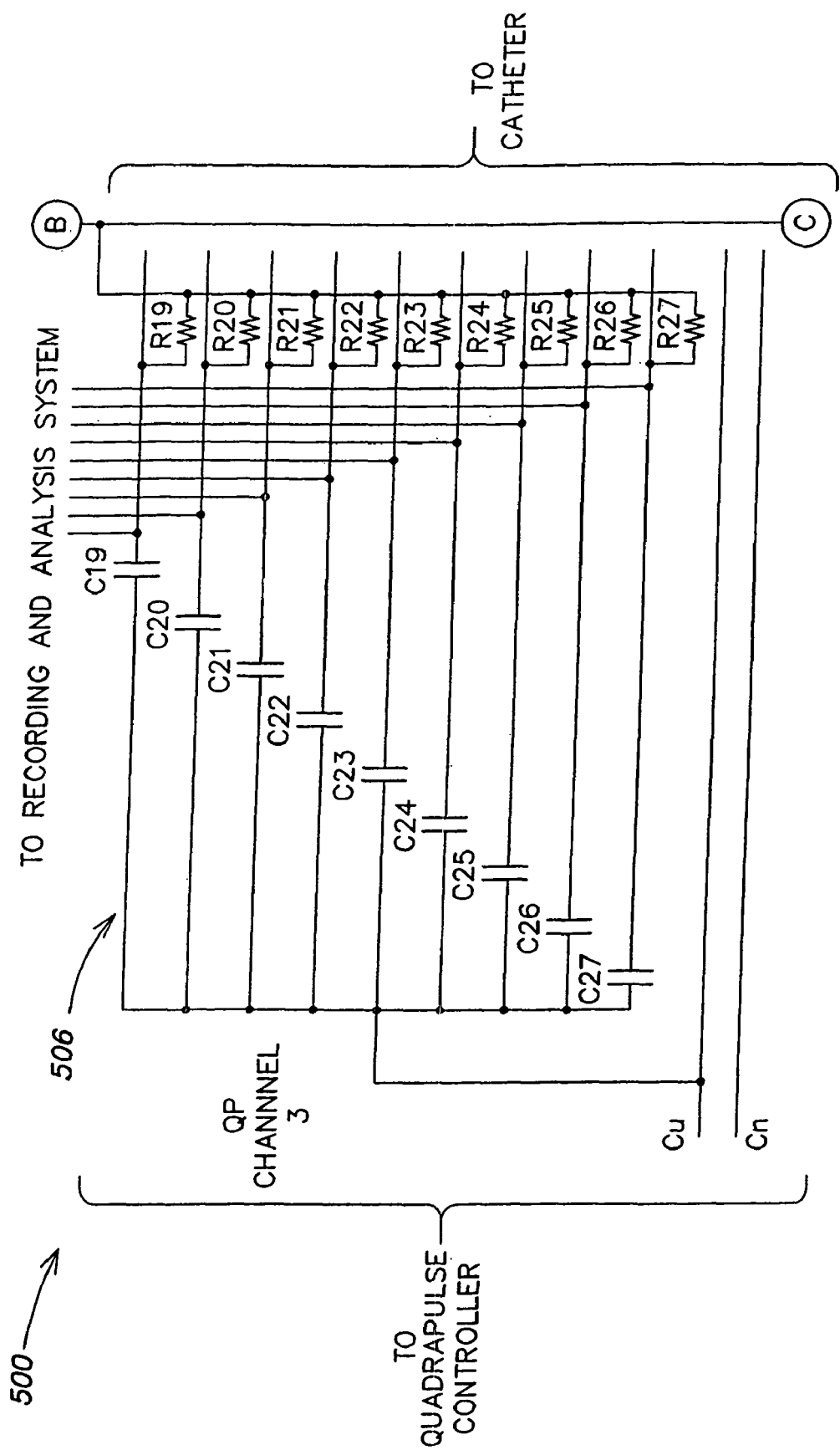
Figure 25D:
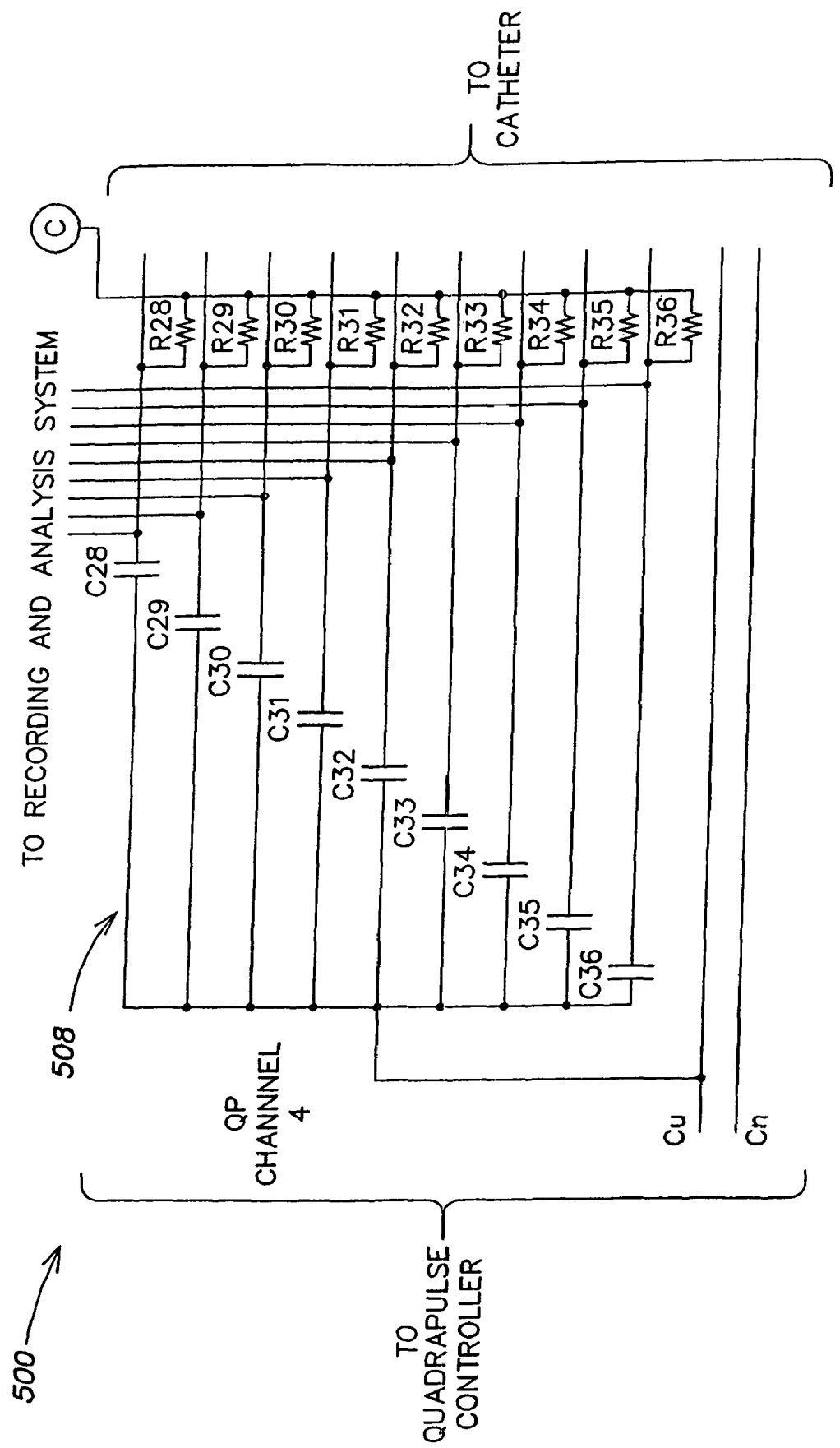

Reference is now made to FIGS. 22, 23, and 24, which figures illustrate how the catheter of the present invention may be used in endocardial and epicardial applications.

Referring to FIG. 22, this figure illustrates an endocardial ablation procedure. In this procedure, catheter shaft 12 is introduced into a patient's heart 150. Appropriate imaging guidance (direct visual assessment, camera port, fluoroscopy, echocardiographic, magnetic resonance, etc.) can be used. FIG. 22 in particular illustrates catheter shaft 12 being placed in the left atrium of the patient's heart. Once catheter shaft 12 reaches the patient's left atrium, it may then be introduced through an ostium 152 of a pulmonary vein 154. As illustrated, braided conductive member 28 is then expanded to its deployed position, where, in the illustrated embodiment, braided conductive member 28 forms a disk. Catheter shaft 12 then advanced further into pulmonary vein 154 until the distal side 156 of braided conductive member 28 makes contact with the ostium of pulmonary vein 154. External pressure may be applied along catheter shaft 12 to achieve the desired level of contact of braided conductive member 28 with the ostium tissue. Energy is then applied to the ostium tissue 152 in contact with braided conductive member 28 to create an annular lesion at or near the ostium. The energy used may be RF (radiofrequency), DC, microwave, ultrasonic, cryothermal, optical, etc.

Reference is now made to FIG. 23, which figure illustrates an epicardial ablation procedure. As illustrated in FIG. 23, catheter shaft 12 is introduced into a patient's thoracic cavity and directed to pulmonary vein 154. Catheter 10 may be introduced through a trocar port or intraoperatively during open chest surgery Using a steering mechanism, preformed shape, or other means by which to make contact between braided conductive member 128 and the outer surface 158 of pulmonary vein 154, braided conductive member 28 is brought into contact with the outer surface 158 of pulmonary vein 154. Appropriate imaging guidance (direct visual assessment, camera port, fluoroscopy, echocardiographic, magnetic resonance, etc.) can be used. As illustrated in FIG. 23, in this procedure, braided conductive member 28 remains in its undeployed or unexpanded condition. External pressure may be applied to achieve contact between braided conductive member 28 with pulmonary vein 154. Once the desired contact with the outer surface 158 of pulmonary vein 154 is attained, ablation energy is applied to surface 158 via braided conductive member 28 using, for example, RF, DC, ultrasound, microwave, cryothermal, or optical energy. Thereafter, braided conductive member 28 may be moved around the circumference of pulmonary vein 154, and the ablation procedure repeated. This procedure may be used to create, for example, an annular lesion at or near the ostium.

Use of the illustrated endocardial or epicardial procedures may be easier and faster than using a single "point" electrode since a complete annular lesion may be created in one application of RF energy.

Reference is now made to FIG. 24 which figure illustrates an endocardial mapping procedure. In the procedure illustrated in FIG. 24, catheter shaft 12 is introduced into pulmonary vein 154 in the manner described in connection with FIG. 22. Once braided conductive 28 has reached a desired location within pulmonary vein 154, braided conductive member 28 is expanded as described in connection with, for example, FIGS. 2-5 until filaments 34 contact the inner wall 160 of pulmonary vein 154. Thereafter, electrical activity within pulmonary vein 154 may be detected, measured, and recorded by an external device connected to the filaments 34 of braided conductive member 28.

Access to the patient's heart can be accomplished via percutaneous, vascular, surgical (e.g. open-chest surgery), or transthoracic approaches for either endocardial or epicardial mapping and/or mapping and ablation procedures.

The present invention is thus able to provide an electrophysiology catheter capable of mapping and/or mapping and ablation operations. In addition, the catheter of the invention may be used to provide high density maps of a tissue region because electrocardiograms may be obtained from individual filaments 34 in braided conductive member 28 in either a bipolar or unipolar mode.

Furthermore, the shape of the electrode region can be adjusted by controlling the radial expansion of braided conductive member 28 so as to improve conformity with the patient's tissue or to provide a desired mapping or ablation profile. Alternatively, braided conductive member 28 may be fabricated of a material of sufficient flexural strength so that the tissue is preferentially conformed to match the expanded or partially expanded shape of the braided conductive member 28.

The catheter of the present invention may be used for mapping procedures, ablation procedures, and temperature measurement and control on the distal and/or proximal facing sides of braided conductive member 28 in its fully expanded positions as illustrated in, for example, FIG. 1. In addition, the catheter of the present invention can be used to perform "radial" mapping procedures, ablation procedures, and temperature measurement and control. That is, the outer circumferential edge 76, illustrated, for example, in FIG. 8, can be applied against an inner circumferential surface of a blood vessel.

Furthermore, being able to use the same catheter for both mapping and ablation procedures has the potential to reduce procedure time and reduce X-ray exposure.

The ability to expand braided conductive member 28 in an artery or vein against a tissue structure such as a freewall or ostium can provide good contact pressure for multiple electrodes and can provide an anatomical anchor for stability. Temperature sensors can be positioned definitively against the endocardium to provide good thermal conduction to the tissue. Lesions can be selectively produced at various sections around the circumference of braided conductive member 28 without having to reposition catheter 10. This can provide more accurate lesion placement within the artery or vein.

Braided conductive member 28, in its radially expanded position as illustrated in particular in FIGS. 1 and 8 is advantageous because, in these embodiments, it does not block the blood vessel during a mapping or ablation procedure, but allows blood flow through the braided conductive member thus allowing for longer mapping and/or ablation times, which can potentially improve accuracy of mapping and efficacy of lesion creation.

Another aspect of the present invention is to provide a method and apparatus for three dimensional mapping of electrical activity in blood vessels and ablation of conductive pathways identified by the three dimensional map.

Figure 26:
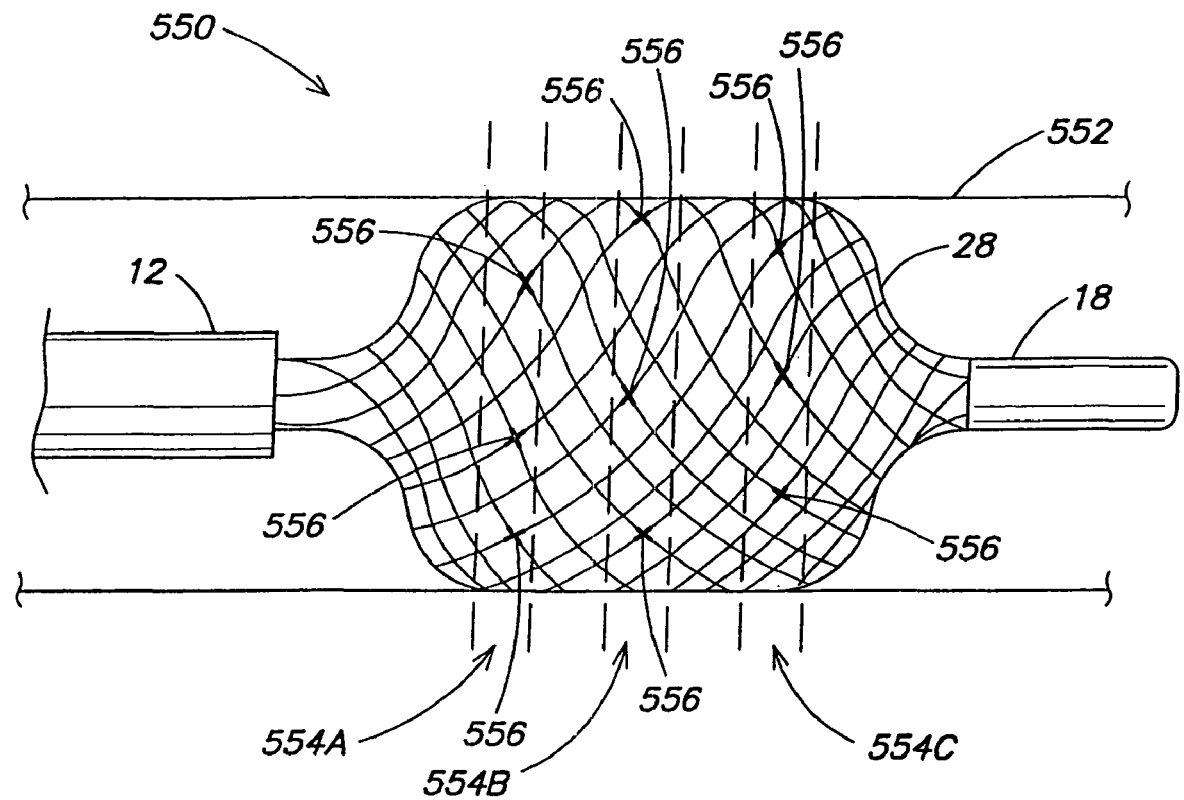
FIG. 26 illustrates another embodiment of the catheter of the present invention.

Reference is now made to FIG. 26, which figure illustrates another embodiment of catheter 10. In the embodiment 550 illustrated in FIG. 26, catheter 10 is illustrated as being disposed inside a blood vessel 552. In the embodiment illustrated in FIG. 26, in the expanded or deployed configuration, braided conductive member 28 has a cylindrical shape. Insulation on filaments 34 that make up braided conductive member 28 is preferentially stripped so as to create one or more circumferential bands 554A, 554B, 554C of regions where the stripped portions of filaments 34 intersect. The stripped portions of filaments 34, where they intersect with other stripped portions, form a series of contact points 556. Each of contact points 556 is electrically isolated from each other. Stripping the insulation so as to create contact points 556 when braided conductive member 28 is in a expanded configuration may be accomplished using the methods previously described. Alternatively, a single band of stripped filaments may be created and then these filaments may be moved lengthwise with respect to each other to create, for example, bands 554A, 554B, 554C.

When brought into contact with the inner circumferential surface of blood vessel 552, contact points 556 can be used to independently sense electrically activity along the wall of the blood vessel.

When used in connection with the circuitry illustrated in FIG. 25 to interface with controller 8, and recording device 2 illustrated in FIG. 1, a cylindrical or three dimensional map of electrical activity sensed by braided conductive member 28 may be obtained.

Any number of contact points 556 may be created in braided conductive member 28 depending upon the number of wires used to create the braided conductive member. The embodiment of the catheter illustrated in FIG. 26 allows, within a single heartbeat, using an electrophysiology recording system, the capture and creation of three dimensional activation and isopotential maps of the electrical activity being sensed by contact points 556. In one embodiment, contact points 556 may be spaced 5 mm from each other along the length of braided conductive member 28 in its expanded configuration.

Once a three dimensional or cylindrical map of the electrical activity sensed by contact points 556 is created, ablation may be then selectively carried out to block or destroy the undesired conduction paths.

Figure 27:
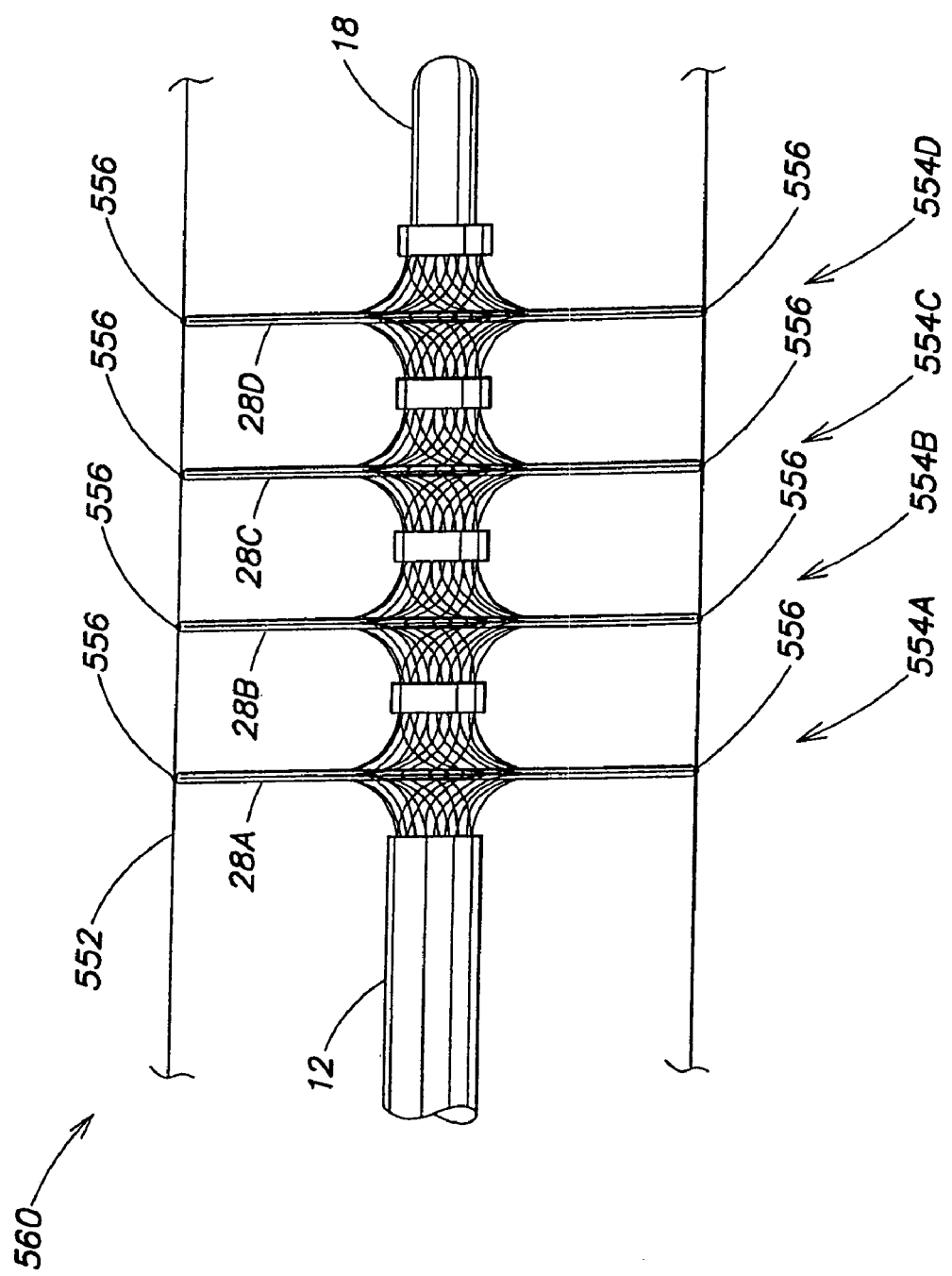
FIG. 27 illustrates another embodiment of the catheter of the present invention.

FIG. 27 illustrates another embodiment of a catheter 10 that may be used to create three dimensional or cylindrical activation and isopotential maps of electrical activity. The embodiment 560 illustrated in FIG. 27 is similar to the multiple braided conductive member embodiment illustrated in FIG. 14. In the embodiment 560, catheter 10 has four braided conductive members 28A, 28B, 28C, and 28D. Each of the braided conductive members 28A-28D is constructed as previously described to provide contact points 556 around the outer circumferential surface of each of braided conductive members 28A-28D. As a result, a number of bands 554A-554D may be created which would allow simultaneous measurement of electrical activity sensed at contact points 556.

Figure 28:
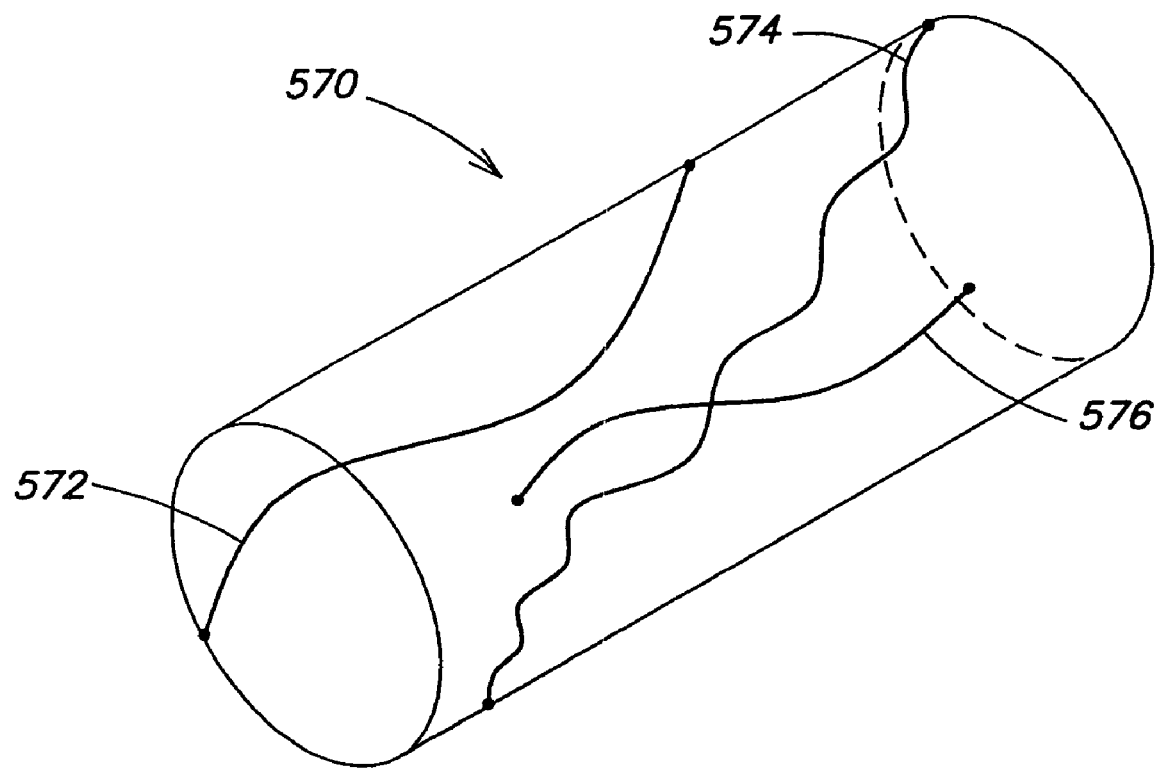
FIG. 28 illustrates a three dimensional or cylindrical map of electrical activation.
Figure 29:
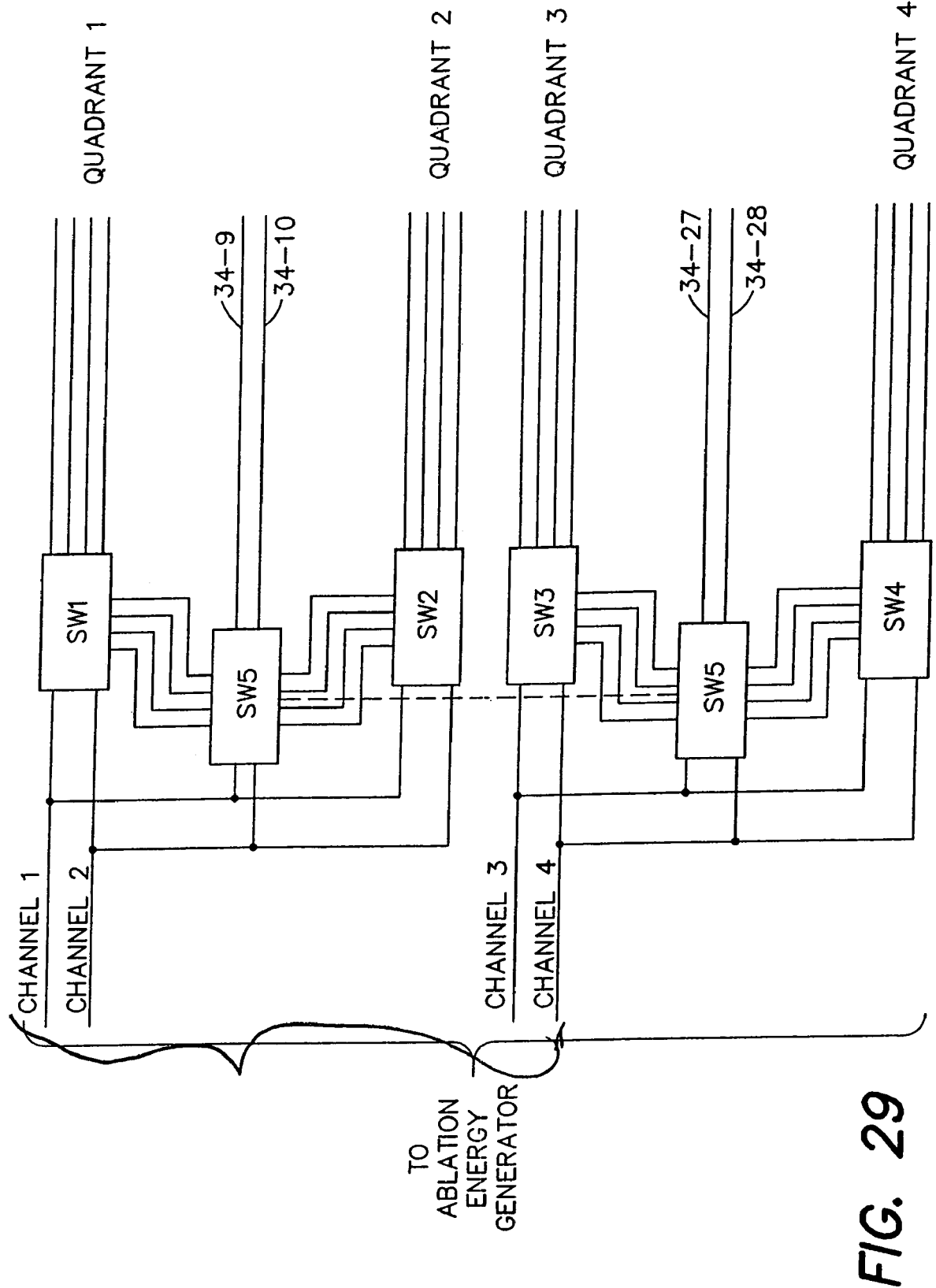
FIGS. 29 and 30A-30D illustrates another embodiment of control circuitry that may be used in connection with the controller.
Figure 30A:
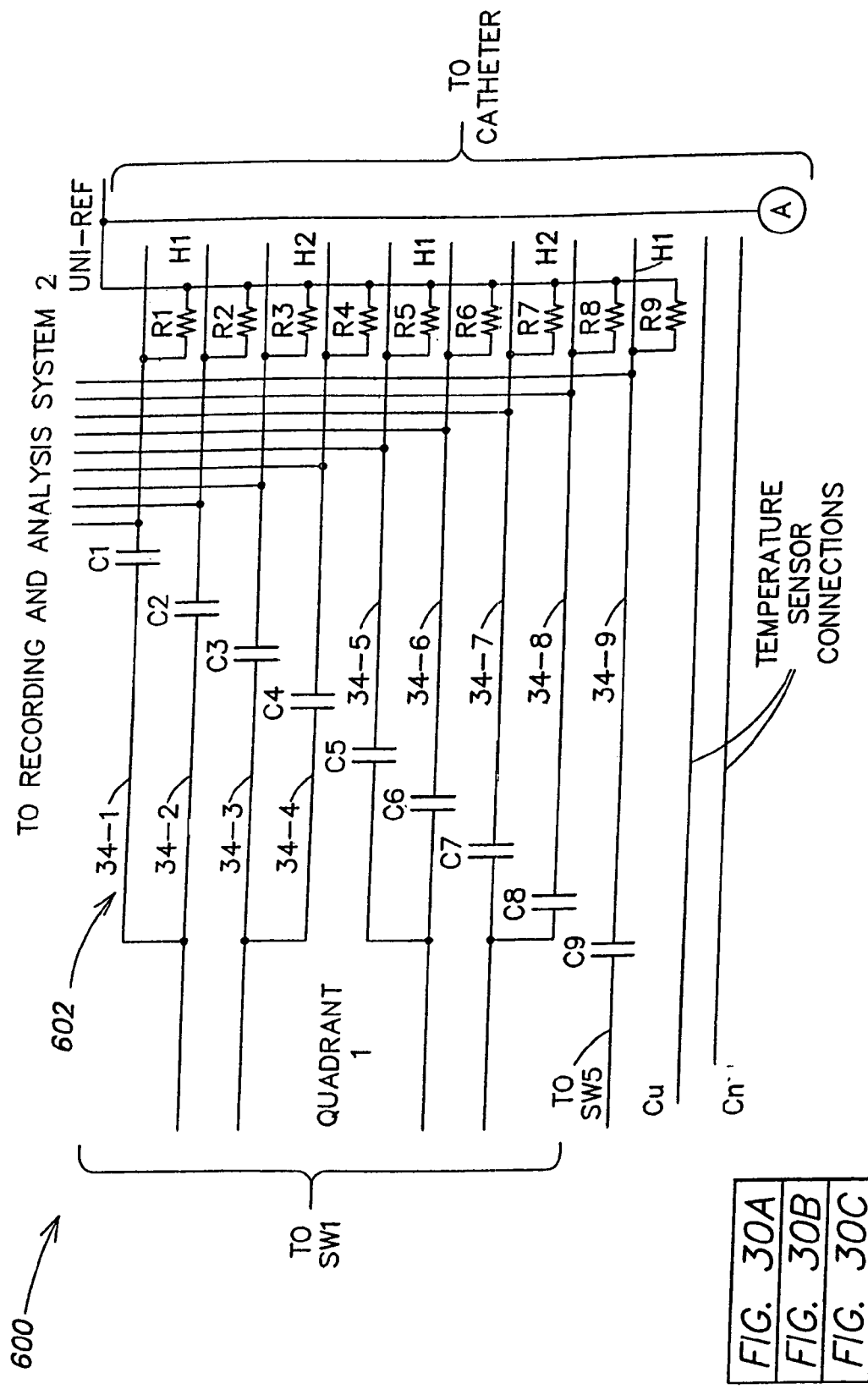
Figure 30B:
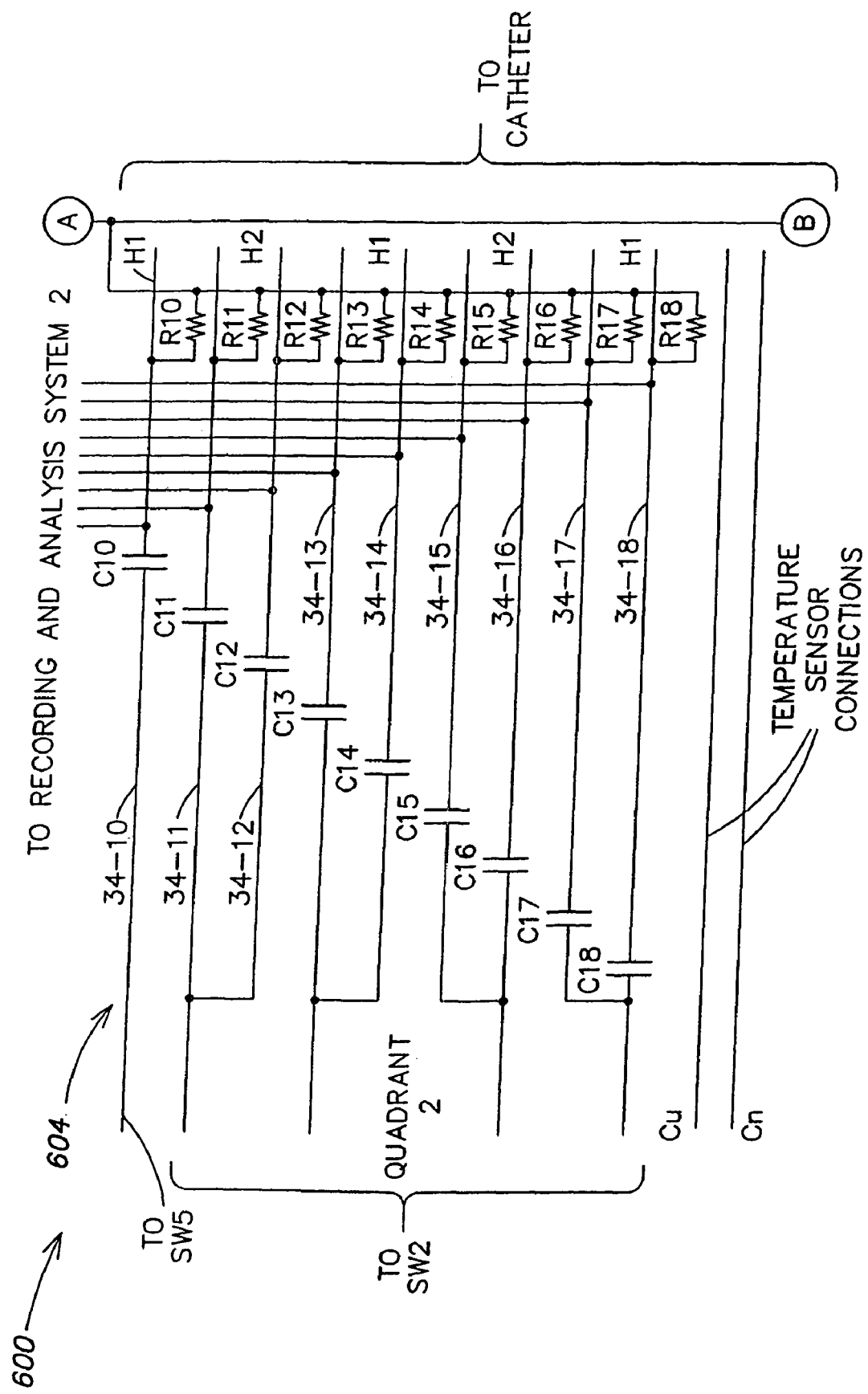
Figure 30C:
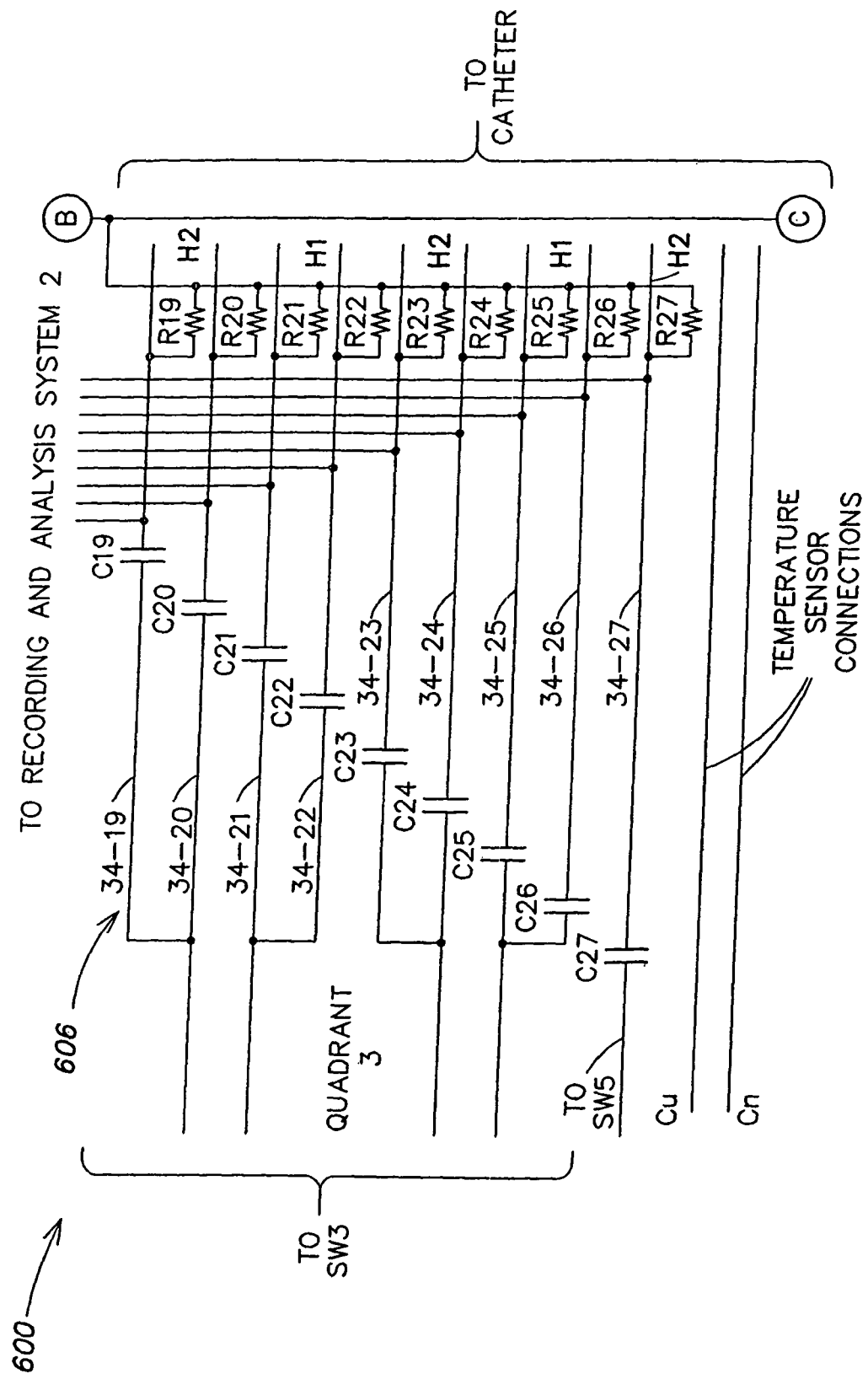
Figure 30D:
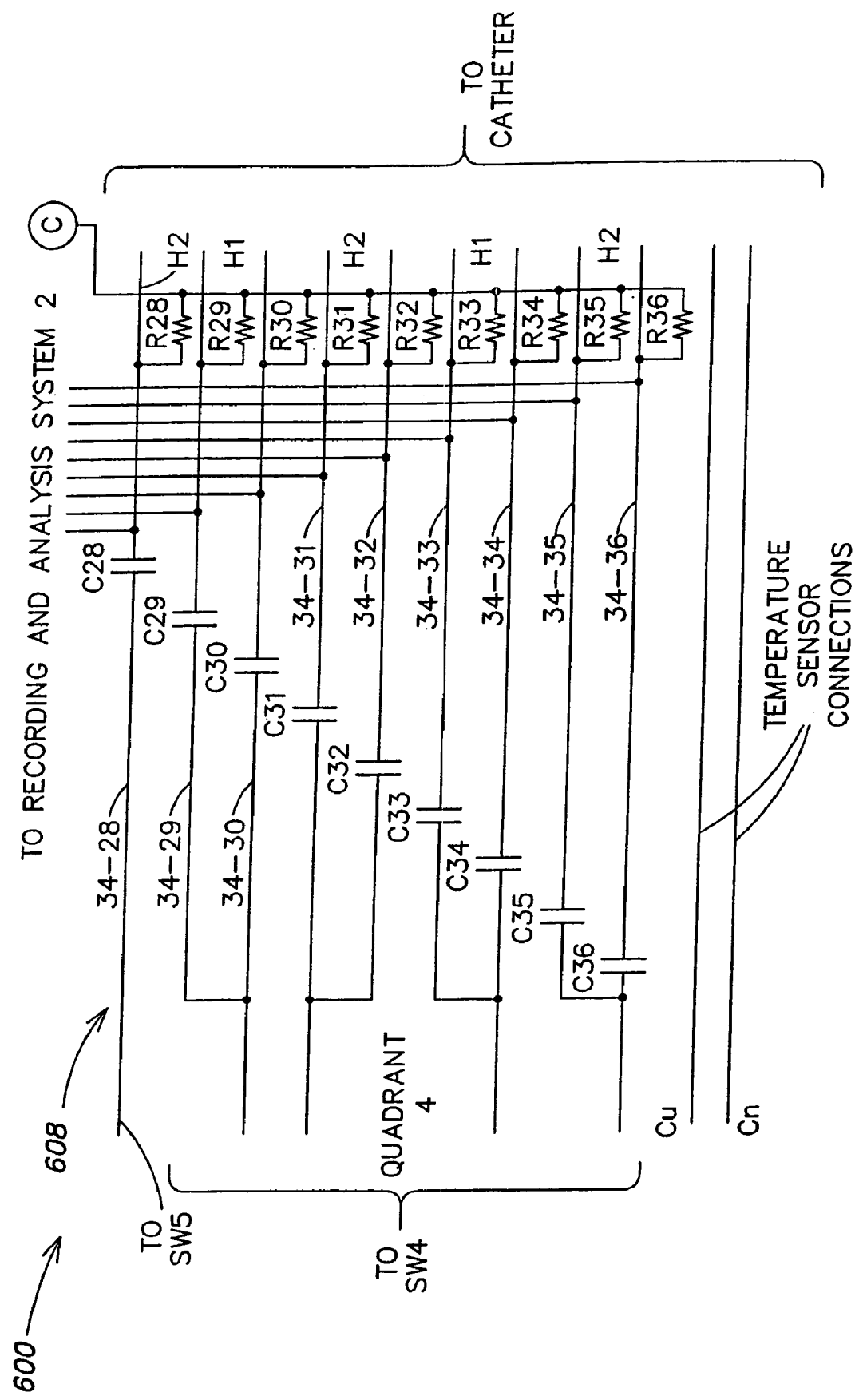

Reference is now made to FIG. 28, which figure illustrates a three dimensional or cylindrical map of the electrical activation sensed by contact points 556 of the catheters illustrated, for example, FIGS. 27 and 28. The map 570 illustrated in FIG. 28 may be generated by recording device 2 of FIG. 1 and may be displayed on, for example, a conventional CRT monitor or provided in printed form to a user. The activation map 570 is a three dimensional or cylindrical map of the electrical activation sensed by the catheter of the inner circumferential surface of blood vessel 552. Map 570 illustrates, for example, three electrical pathways sensed by the catheters of FIGS. 26 and 27 during simultaneous acquisition, within a single heartbeat, of the electrical activity along the length of blood vessel 552. In particular, cylindrical or three dimensional map 570 illustrates a first electrical conduction pathway 572, a second electrical conduction pathway 574 and a third electrical conduction pathway 576. Through appropriate timing and synchronization control of recording device 2, the map 570 can illustrate the direction of conduction as well as the location of the conduction pathways.

The techniques and systems described in application Ser. No. 09/943,408, entitled Software Controlled Electrophysiology Data Management, and incorporated herein by reference, may be used in the present invention.

Thereafter, during an ablation procedure, a physician can pace from different sites and observe which of electrical conduction pathways 572, 574, 576 is activated as a result of the pacing signal. If one of the electrical conduction pathways 572, 574, 576 is identified as a pathway that allows errant electrical signals to cause a cardiac arrhythmia, one of the contact points 556 can be selectively chosen using the circuitry of FIG. 25 in connection with controller 8 and ablation energy generator 4 to block or destroy the conduction pathway that is involved in the arrhythmia. Thereafter, another electrical activation map can be generated in response to a later pacing signal to determine if the electrical conduction pathway that is allowing the arrhythmic generating pulse to enter the heart has been blocked or disrupted. This process can continue interatively until therapeutic disconnection of the electrical conduction path is achieved. Therapeutic disconnection means a complete block, a partial block, or any therapeutically effective change in conduction properties of the tissue.

Thereafter, a pacing signal can be introduced at another site and another cylindrical or three dimensional activation map can be generated. If this subsequent pacing signal indicates that another of electrical conduction paths 572, 574, or 576 is involved, then selective ablation can be applied to that path to therapeutically block or destroy it.

This process can be carried out repeatedly until all of the electrical conduction pathways that allow arrhythmia generating signals to enter the heart are therapeutically blocked or destroyed.

This method has advantages in that only the electrical conduction pathways that are involved in arrhythmia generating signals are ablated thus allowing for a more focused approach in that only the tissue necessary to be ablated to block the errant electrical signals in destroyed, the rest of the inner lining of blood vessel 552 does not need to be operated upon.

It will be appreciated that in addition to using a pacing signal, the method and apparatus of the invention may be used to simply generate a map in response to a naturally occurring arrhythmia and once the electrical pathway is identified, that pathway can then be selectively ablated.

Selectively choosing a particular contact point 556 for ablation or mapping can make use of the sectoring methods and apparatus previously described.

A location sensor and system may be used to determine and repeat the exact orientation of the catheter and contact points 556 in blood vessel 552. Alternatively, radiopaque or fluoroscopic markers may be disposed on the filaments 34 that make up braided conductive member 28 so that the location of the contact points 556 may be determined.

The method and apparatus illustrated in FIGS. 26-28 is particularly useful for measuring electrical activation in and for ablation of the cardiac muscle sleeve that provides the interface between a chamber of the heart, such as one of the atria and a vein, such as one of the pulmonary veins.

Having thus described at least one illustrative embodiment of the invention, various alterations, modifications, and improvements will readily occur to those skilled in the art. For example, one skilled in the art will appreciate that each of the above described features may be selectively combined into a method of use and/or a device depending on, for example, the function desired to be carried out. Such alterations, modifications, and improvements are intended to be within the spirit and scope of the invention. Accordingly, the foregoing description is by way of example only and is not intended as limiting. The invention is limited only as defined in the following claims and the equivalents thereto.

The invention claimed is:

1. A device for routing ablation energy to and for routing mapping signals received from an electrophysiology catheter having a plurality of conductive filaments comprising first and second filaments, the device comprising:

circuitry that provides an electrical signal path between the first and second filaments that has a low impedance when the first and second filaments are used to transmit ablation energy and a higher impedance when the first and second filaments are used to transmit mapping signals.

2. The device of claim 1 further comprising switching circuitry for selectively coupling filaments in the electrophysiology catheter to a source of ablation energy.

3. The device of claim 2, wherein the switching circuitry selectively couples sectors of filaments to a source of ablation energy.

4. The device of claim 3, wherein there are four sectors.

5. The device of claim 2, wherein the switching circuitry selectively couples approximately a first half of the filaments in the electrophysiology catheter to a source of ablation energy.

6. The device of claim 5, wherein the switching circuitry selectively couples approximately a second half of the filaments in the electrophysiology catheter to a source of ablation energy.

7. The device of claim 6, wherein the first half of the filaments is interleaved with the second half of the filaments.

8. The device of claim 1, wherein the circuitry comprises a capacitor in the electrical signal path of each conductive filament.

9. The device of claim 1, further comprising a resistor respectively coupled to each conductive filament.

10. A catheter system comprising an electrophysiology catheter, an ablation energy generator, a recording device, and a device according to claim 1 that couples the electrophysiology catheter to the ablation energy generator and the recording device.

* * * * *